United States Patent [19]
Covello et al.

[11] Patent Number: 6,153,815
[45] Date of Patent: Nov. 28, 2000

[54] DNA SEQUENCES FROM BRASSICACEAE ENCODING SQUALENE EPOXIDASE AND PROCESS OF RAISING SQUALENE LEVELS IN PLANTS THEREWITH

[75] Inventors: Patrick S. Covello; Martin J. T. Reaney; Samuel L. MacKenzie, all of Saskatoon, Canada

[73] Assignee: National Research Council of Canada, Ottawa, Canada

[21] Appl. No.: 09/147,009

[22] PCT Filed: Mar. 13, 1997

[86] PCT No.: PCT/CA97/00175

§ 371 Date: Jan. 5, 1999

§ 102(e) Date: Jan. 5, 1999

[87] PCT Pub. No.: WO97/34003

PCT Pub. Date: Sep. 18, 1997

Related U.S. Application Data

[60] Provisional application No. 60/013,340, Mar. 13, 1996.

[51] Int. Cl.[7] .............................. A01H 5/00; A01H 5/10; C12N 15/29; C12N 15/52; C12N 15/82
[52] U.S. Cl. ..................... 800/306; 435/320.1; 536/23.2; 536/23.6; 800/278; 800/298
[58] Field of Search ................................ 435/69.1, 320.1, 435/419, 468; 536/23.2, 23.6; 800/278, 281, 286, 298, 306

[56] References Cited

U.S. PATENT DOCUMENTS 5,349,126  9/1994  Chappell et al. ....................... 800/205

FOREIGN PATENT DOCUMENTS 06 090 743  4/1994  Japan .
WO 96 09393 A  3/1996  WIPO .

OTHER PUBLICATIONS

Sakakibara J, et al. "Molecular cloning and expression of rat squalene epoxidase." JBC 1: 17–20, Jan. 1995.

Kosuga K, et al. "Nucleotide sequence of a cDNA for mouse squalene epoxidase." Biochim. Biophys. Acta 1260: 345–348, 1995.

De Block M. "The cell biology of plant transformation: Current state, problems, prospects and the implications for the plant breeding." Euphytica 71: 1–14, 1993.

EMBL Database, Feb. 4, 1995, Heidelberg, XP002033788 Newman T. et al.: "AC T44667".

EMBL Database, May 27, 1996, Heidelberg, XP002033789 Newman T. et al.: "AC W43353".

Jandrositz A. et al., "The gene encoding squalene epoxidase from Saccharomyces cerevisiae: cloning and characterization", GENE, vol. 107, No. 1, 1991, pp. 155–160 XP002033661.

EMBL Database, Mar. 7, 1996, Heidelberg XP002033786, Newman T. et al.: "AC N64916".

EMBL Database, Mar. 18, 1995 Heidelberg, XP002033787 De Loo F. et al.: "AC T15019".

*Primary Examiner*—Amy Nelson

[57] ABSTRACT

The invention provides DNA isolated from a plant species of the family Brassicaceae that can be introduced into the genomes of plants to produce genetically-modified plants having higher levels of squalene than the natural plants. The DNA corresponds to squalene epoxidase gene of the same or a related plant, and may have the sequence as shown by SEQ ID NO:1, SEQ ID NO:3, or SEQ ID NO:5, or a sequence having at least 60% identity with such a sequence. The DNA is introduced into the genome in a way that results in down-regulation of an exogenous plant squalene gene to suppress the expression of squalene epoxidase. The invention also relates to a process of producing genetically-modified plants, plasmids and vectors used in the method, genetically-modified plants and seeds thereof and a method of producing squalene from the modified plants.

41 Claims, 8 Drawing Sheets

FIG. 1A

|  | | | | | | | | | | | 10 | | | | | | | | | | 20 | |
|---|---|---|---|---|---|---|---|---|---|---|---|---|---|---|---|---|---|---|---|---|---|---|
| B. NAPUS 111 | M | - | - | - | - | - | - | - | - | - | - | - | - | - | - | - | - | - | - | - | - | 2 |
| B. NAPUS 411 | M | - | - | - | - | - | - | - | - | - | - | - | - | - | - | - | - | - | - | - | - | 2 |
| ARABIDOPSIS | M | - | - | - | - | - | - | - | - | - | - | - | - | - | - | - | - | - | - | - | - | 2 |
| MOUSE | M | W | T | F | L | G | I | A | T | F | T | Y | F | Y | K | K | C | G | D | V | | 20 |
| RAT | M | W | T | F | L | G | I | A | T | F | T | Y | F | Y | K | K | C | G | D | V | | 20 |
| YEAST | M | - | - | - | - | - | - | - | - | - | - | - | - | - | - | - | - | - | - | - | - | 2 |

|  | | | | | | | | | 30 | | | | | | | | | 40 | |
|---|---|---|---|---|---|---|---|---|---|---|---|---|---|---|---|---|---|---|---|
| B. NAPUS 111 | - | - | - | - | - | - | - | - | - | - | - | - | - | - | - | - | - | - | 2 |
| B. NAPUS 411 | - | - | - | - | - | - | - | - | - | - | - | - | - | - | - | - | - | - | 2 |
| ARABIDOPSIS | - | - | - | - | - | - | - | - | - | - | - | - | - | - | - | - | - | - | 2 |
| MOUSE | T | L | A | N | K | E | L | L | L | C | V | L | V | F | L | S | L | G | L | V | 40 |
| RAT | T | L | A | N | K | E | L | L | L | C | V | L | V | F | L | S | L | G | L | V | 40 |
| YEAST | - | - | - | - | - | - | - | - | - | - | - | - | - | - | - | - | - | - | 2 |

|  | | | | | | | | | 50 | | | | | | | | | 60 | |
|---|---|---|---|---|---|---|---|---|---|---|---|---|---|---|---|---|---|---|---|
| B. NAPUS 111 | - | - | - | - | - | - | - | - | - | - | - | - | - | - | - | - | - | - | 2 |
| B. NAPUS 411 | - | - | - | - | - | - | - | - | - | - | - | - | - | - | - | - | - | - | 2 |
| ARABIDOPSIS | - | - | - | - | - | - | - | - | - | - | - | - | - | - | - | - | - | - | 2 |
| MOUSE | L | S | Y | R | C | R | H | R | H | G | G | L | L | G | R | H | Q | S | G | A | 60 |
| RAT | L | S | Y | R | C | R | H | R | N | G | G | L | L | G | R | H | Q | S | G | S | 60 |
| YEAST | - | - | - | - | - | - | - | - | - | - | - | - | - | - | - | - | - | - | 2 |

|  | | | | | | | | | 70 | | | | | | | | | 80 | |
|---|---|---|---|---|---|---|---|---|---|---|---|---|---|---|---|---|---|---|---|
| B. NAPUS 111 | D | M | A | F | V | E | V | C | C | L | R | M | L | L | V | F | V | L | S | W | T | T | 21 |
| B. NAPUS 411 | D | L | Y | A | A | F | P | H | V | C | C | L | W | T | L | L | A | F | V | L | T | W | T | 21 |
| ARABIDOPSIS | T | Y | A | W | - | - | - | - | - | L | W | T | L | L | A | F | V | L | T | W | W | M | 17 |
| MOUSE | Q | F | A | A | F | S | D | I | L | S | A | L | P | L | I | G | F | F | W | A | 80 |
| RAT | Q | F | A | A | F | S | S | D | I | L | S | A | L | P | L | I | G | F | F | W | A | 80 |
| YEAST | - | - | - | - | - | - | - | - | - | - | - | - | - | - | - | - | - | - | 2 |

|  | | | | | | | | | 90 | | | | | | | | | 100 | |
|---|---|---|---|---|---|---|---|---|---|---|---|---|---|---|---|---|---|---|---|
| B. NAPUS 111 | I | F | - | - | - | - | - | - | - | H | V | N | N | R | K | K | K | K | A | 33 |
| B. NAPUS 411 | V | F | - | - | - | - | - | - | - | Y | V | N | N | N | R | R | K | K | - | V | 32 |
| ARABIDOPSIS | V | F | - | - | - | - | - | - | - | H | L | I | K | M | K | K | A | A | T | 29 |
| MOUSE | K | S | P | - | E | S | E | K | K | E | Q | L | E | S | K | K | C | R | R | K | E | 99 |
| RAT | K | S | P | P | E | S | E | K | K | E | Q | L | E | S | K | R | R | K | E | 100 |
| YEAST | - | - | - | - | - | - | - | - | - | - | - | - | - | - | - | - | - | - | - | 2 |

|  | | | | | | | | | 110 | | | | | | | | | 120 | |
|---|---|---|---|---|---|---|---|---|---|---|---|---|---|---|---|---|---|---|---|
| B. NAPUS 111 | T | K | L | A | D | L | A | T | E | E | R | K | E | G | - | - | - | - | - | - | 48 |
| B. NAPUS 411 | A | G | K | L | P | D | A | A | T | E | E | V | R | R | D | G | - | - | - | - | - | - | 47 |
| ARABIDOPSIS | G | D | L | - | E | A | E | A | E | E | A | R | R | D | G | - | - | - | - | - | - | 43 |
| MOUSE | I | G | L | S | E | T | T | L | T | G | A | A | T | S | V | S | T | S | F | V | 119 |
| RAT | V | N | L | S | E | T | T | L | T | G | A | A | T | S | V | S | T | S | S | V | 120 |
| YEAST | - | - | - | - | S | A | V | N | V | A | P | E | L | I | N | A | D | N | T | 16 |

|  | | | | | | | | | 130 | | | | | | | | | 140 | |
|---|---|---|---|---|---|---|---|---|---|---|---|---|---|---|---|---|---|---|---|
| B. NAPUS 111 | - | G | P | D | V | I | I | V | G | A | G | V | G | G | S | A | L | A | Y | A | 66 |
| B. NAPUS 411 | - | D | A | D | V | I | I | V | G | A | G | V | G | G | S | A | L | A | Y | A | 65 |
| ARABIDOPSIS | - | A | T | D | V | I | I | V | G | A | G | V | A | G | A | S | L | A | Y | A | 61 |
| MOUSE | T | D | P | E | V | I | I | V | G | S | G | V | L | G | S | A | L | A | A | V | 139 |
| RAT | T | D | P | E | V | I | I | I | G | S | G | V | L | G | S | A | L | A | T | V | 140 |
| YEAST | I | T | Y | D | A | I | V | I | G | A | G | V | I | G | P | C | V | A | T | G | 36 |

| | | | | | | | | | | | | | | | |
|---|---|---|---|---|---|---|---|---|---|---|---|---|---|---|---|
| | | | | | 290 | | | | | | | 300 | | | |
| B. NAPUS 111 | L | I | E | E | K | G | V | V | K | G | V | T | Y | K | N | S | S | G | E | E | 196 |
| B. NAPUS 411 | L | I | E | E | K | G | V | I | K | G | V | T | Y | K | N | S | S | A | G | E | E | 195 |
| ARABIDOPSIS | L | I | E | E | E | G | V | V | K | G | V | T | Y | K | N | S | S | A | G | E | E | 191 |
| MOUSE | L | L | E | E | D | D | A | V | V | I | G | V | Q | Y | K | D | K | E | T | G | D | 270 |
| RAT | L | L | E | E | D | D | A | N | V | I | G | V | Q | Y | K | D | K | E | T | G | D | 271 |
| YEAST | I | L | K | D | E | K | N | E | V | V | G | A | K | V | D | I | D | G | R | G | 196 |

| | | | | | 310 | | | | | | | 320 | | | |
|---|---|---|---|---|---|---|---|---|---|---|---|---|---|---|---|
| B. NAPUS 111 | T | T | S | F | - | A | P | L | T | V | V | C | D | G | C | H | S | N | L | R | 215 |
| B. NAPUS 411 | T | T | A | F | - | A | P | L | T | V | V | C | D | G | C | Y | S | N | L | R | 214 |
| ARABIDOPSIS | I | T | A | F | - | A | P | L | T | V | V | C | D | G | C | Y | S | N | L | R | 210 |
| MOUSE | T | K | E | L | H | A | P | L | T | V | V | A | D | G | L | F | S | K | F | R | 290 |
| RAT | T | K | E | L | H | A | P | L | T | V | V | A | D | G | L | F | S | K | F | R | 291 |
| YEAST | K | V | E | F | K | A | H | L | T | F | I | C | D | G | I | F | S | R | F | R | 216 |

| | | | | | 330 | | | | | | | 340 | | | |
|---|---|---|---|---|---|---|---|---|---|---|---|---|---|---|---|
| B. NAPUS 111 | R | S | L | N | D | N | N | A | E | V | T | A | Y | E | - | I | G | Y | I | S | 234 |
| B. NAPUS 411 | R | S | V | N | D | N | N | A | A | E | V | I | A | Y | Q | - | V | G | Y | V | S | 233 |
| ARABIDOPSIS | R | S | L | V | D | N | T | E | E | V | L | S | Y | M | - | V | G | Y | V | T | 229 |
| MOUSE | K | S | L | I | S | N | K | K | V | S | - | V | S | H | F | V | G | F | L | M | 309 |
| RAT | K | N | L | I | S | N | D | K | K | V | S | - | V | S | H | F | V | G | F | I | M | 310 |
| YEAST | K | E | L | H | P | D | H | V | P | T | V | G | S | S | F | V | G | M | S | L | 236 |

| | | | | | 350 | | | | | | | 360 | | | |
|---|---|---|---|---|---|---|---|---|---|---|---|---|---|---|---|
| B. NAPUS 111 | R | N | C | R | L | E | Q | P | D | K | L | H | L | I | M | - | A | K | P | S | 253 |
| B. NAPUS 411 | K | N | C | Q | L | E | D | P | E | K | L | K | L | I | M | - | S | K | P | S | 252 |
| ARABIDOPSIS | K | N | S | R | L | E | D | P | H | L | L | H | L | I | F | - | S | K | P | L | 248 |
| MOUSE | K | D | A | P | Q | F | K | P | N | F | A | E | L | V | L | V | - | N | P | S | 328 |
| RAT | K | D | A | P | Q | F | K | A | N | F | A | E | L | V | L | V | - | D | P | S | 329 |
| YEAST | F | N | A | K | N | P | A | P | M | H | G | H | V | I | F | G | S | D | H | M | 256 |

| | | | | | 370 | | | | | | | 380 | | | |
|---|---|---|---|---|---|---|---|---|---|---|---|---|---|---|---|
| B. NAPUS 111 | F | A | M | L | Y | Q | V | S | S | T | D | V | R | C | N | F | E | L | L | S | 273 |
| B. NAPUS 411 | F | T | M | L | Y | Q | I | S | S | T | D | V | R | C | V | M | E | I | F | P | 272 |
| ARABIDOPSIS | V | C | V | I | Y | Q | I | T | S | D | E | V | R | C | V | A | E | V | P | A | 268 |
| MOUSE | P | V | L | I | Y | Q | I | S | S | S | E | E | T | R | V | L | V | D | I | R | G | 348 |
| RAT | P | V | L | I | Y | Q | I | S | P | S | E | E | T | R | V | L | V | D | I | R | G | 349 |
| YEAST | P | I | L | V | Y | Y | Q | I | S | P | E | E | T | T | R | I | L | C | A | Y | N | S | 276 |

| | | | | | 390 | | | | | | | 400 | | | |
|---|---|---|---|---|---|---|---|---|---|---|---|---|---|---|---|
| B. NAPUS 111 | K | N | L | P | S | V | S | N | G | E | M | T | S | F | V | R | N | S | I | A | 293 |
| B. NAPUS 411 | G | N | I | P | S | S | I | S | N | G | E | M | M | A | V | Y | L | K | N | S | T | M | A | 292 |
| ARABIDOPSIS | D | S | I | P | S | I | I | S | N | G | E | M | M | T | F | L | K | N | K | S | M | A | 288 |
| MOUSE | - | E | L | P | R | - | - | - | - | N | L | R | E | Y | M | A | E | Q | Q | I | Y | 363 |
| RAT | - | E | L | P | R | - | - | - | - | N | L | R | E | Y | M | T | I | E | Q | Q | I | Y | 364 |
| YEAST | P | K | V | P | A | - | - | - | - | D | I | K | S | W | M | I | K | D | I | V | Q | 292 |

| | | | | | 410 | | | | | | | 420 | | | |
|---|---|---|---|---|---|---|---|---|---|---|---|---|---|---|---|
| B. NAPUS 111 | P | Q | V | P | L | - | - | K | L | R | K | T | F | L | K | G | L | D | E | G | 311 |
| B. NAPUS 411 | P | Q | V | P | P | - | - | E | L | R | K | I | F | L | K | K | G | I | D | E | G | 310 |
| ARABIDOPSIS | P | Q | I | P | E | T | G | N | L | R | E | I | F | L | K | K | G | I | E | E | G | 308 |
| MOUSE | P | Q | L | P | - | - | - | E | H | L | K | E | S | F | L | E | A | S | Q | N | G | 381 |
| RAT | P | Q | I | P | - | - | - | D | H | L | K | E | S | F | L | E | A | C | Q | N | A | 382 |
| YEAST | P | F | I | P | - | - | K | S | L | R | P | S | F | D | E | A | V | S | Q | G | 310 |

FIG. 1D

```
                    430                             440
B. NAPUS 111   -  S  H  I  K  I  T  Q  A  K  R  I  P  A  T  L  S  R  K  K    330
B. NAPUS 411   -  A  Q  I  K  A  M  P  T  K  K  M  E  A  S  T  L  S  E  K  Q  329
ARABIDOPSIS    L  P  E  I  K  A  S  T  A  T  K  S  M  E  A  S  R  L  C  D  K  K  R  328
MOUSE          -  -  R  L  R  T  T  M  P  A  A  S  F  F  Y  L  P  P  S  S  S  V  N  K  K  R  399
RAT            -  -  R  L  R  T  A  M  P  A  A  S  F  F  Y  L  P  P  S  S  S  V  N  K  K  R  400
YEAST          -  -  K  F  R  A  M  P  N  S  Y  L  P  A  R  Q  N  D  V  T    328

450                             460
B. NAPUS 111   G  V  I  V  L  G  D  A  F  N  M  R  H  P  V  I  A  S  G  M    350
B. NAPUS 411   G  V  I  V  L  G  D  A  F  N  M  R  H  P  V  I  I  A  S  G  M  349
ARABIDOPSIS    G  V  I  V  L  G  D  A  F  N  M  R  H  P  L  I  I  A  S  G  M  348
MOUSE          G  V  L  I  L  G  D  A  A  Y  N  L  R  H  P  L  T  G  G  G  M  419
RAT            G  V  L  L  L  G  D  A  A  Y  N  L  R  H  P  L  T  G  G  G  M  420
YEAST          G  M  C  V  I  G  D  A  L  N  M  R  H  P  L  T  G  G  G  M    348

470                             480
B. NAPUS 111   M  V  L  L  S  D  I  L  I  L  S  R  L  L  K  P  L  G  N  L    370
B. NAPUS 411   M  V  V  L  S  D  I  L  I  L  R  R  L  L  Q  P  L  R  N  L    369
ARABIDOPSIS    M  V  A  L  S  D  I  C  I  L  R  N  L  L  K  P  L  P  N  L    368
MOUSE          T  V  A  L  K  D  I  K  L  W  R  Q  L  L  K  D  I  P  D  L    439
RAT            T  V  A  L  K  K  D  I  K  I  W  R  Q  L  L  K  D  I  P  D  L  440
YEAST          T  V  G  L  H  D  V  V  L  L  I  K  K  I  G  D  L  -  D  F    367

490                             500
B. NAPUS 111   G  D  E  N  K  V  S  E  V  M  K  S  F  Y  A  L  R  K  P  M    390
B. NAPUS 411   S  D  A  N  K  V  S  E  V  I  K  S  F  Y  V  I  R  K  P  M    389
ARABIDOPSIS    S  N  T  K  V  S  D  L  V  K  S  F  Y  I  I  R  K  P  M       388
MOUSE          Y  D  D  A  A  I  F  Q  A  K  K  S  F  F  W  S  R  R  R  T    459
RAT            Y  D  D  A  A  I  F  Q  A  K  K  S  F  F  W  S  E  R  R  S  Y  460
YEAST          S  D  R  E  K  V  D  E  L  D  Y  H  F  E  R  K  S  Y          387

510                             520
B. NAPUS 111   S  A  T  V  N  T  L  G  N  S  F  W  Q  V  L  I  A  S  T  D    410
B. NAPUS 411   S  A  T  V  N  T  L  G  N  A  F  S  Q  V  L  I  V  A  S  T  D  409
ARABIDOPSIS    S  A  T  V  N  T  L  A  S  I  F  S  S  Q  V  L  L  V  A  A  T  T  D  408
MOUSE          H  S  F  V  V  N  V  L  A  Q  A  L  Y  E  L  F  S  A  T  D    479
RAT            H  D  S  S  F  V  V  N  V  L  A  Q  A  L  Y  Y  E  L  F  S  A  A  T  D  480
YEAST          D  S  S  -  V  V  I  V  L  S  V  A  L  Y  L  F  A  A  D  S    406

530                             540
B. NAPUS 111   E  A  K  E  A  M  R  Q  G  C  F  D  Y  L  S  S  G  G  F  R    430
B. NAPUS 411   E  A  K  K  E  A  M  M  R  Q  G  C  F  D  Y  Y  L  S  S  G  G  F  R  429
ARABIDOPSIS    E  A  R  E  G  M  R  Q  G  C  F  N  Y  Y  L  A  R  G  D  F  K    428
MOUSE          D  S  L  H  Q  L  R  K  A  C  F  L  Y  F  K  L  G  G  E  C    499
RAT            D  S  L  R  Q  L  R  K  A  C  F  L  Y  F  F  K  L  G  G  E  C    500
YEAST          D  N  L  K  A  L  Q  K  G  C  F  K  Y  F  Q  R  G  G  D  C    426

550                             560
B. NAPUS 111   T  S  G  L  M  A  L  I  G  G  M  N  P  R  P  L  S  L  F  Y    450
B. NAPUS 411   T  S  G  M  M  A  L  L  L  G  G  M  N  P  R  P  L  S  T  L  I  F  449
ARABIDOPSIS    T  R  G  L  M  T  I  L  G  G  M  N  P  H  P  L  T  L  V  L    448
MOUSE          V  T  G  P  V  G  L  L  S  I  L  S  P  H  P  L  V  L  I  R    519
RAT            L  T  G  P  V  G  L  L  S  I  L  S  S  P  D  P  V  L  L  I  R  520
YEAST          V  N  K  P  V  E  F  L  S  G  V  L  P  K  P  L  Q  L  T  R    446
```

| | | | | | | | | 570 | | | | | | | 580 | | |
|---|---|---|---|---|---|---|---|---|---|---|---|---|---|---|---|---|---|
| B. NAPUS 111 | H | L | F | V | I | S | L | S | S | I | G | Q | L | L | S | P | F | P | T | P | 470 |
| B. NAPUS 411 | H | L | C | G | I | T | T | L | S | S | I | G | Q | L | L | S | P | F | P | P | T | S | P | 469 |
| ARABIDOPSIS | H | L | V | A | I | T | A | L | L | S | T | M | G | H | L | L | S | P | F | P | S | S | P | 468 |
| MOUSE | H | F | F | S | V | A | A | I | Y | S | A | A | T | - | - | - | - | - | - | - | - | - | - | 530 |
| RAT | H | F | F | S | V | A | A | V | Y | Y | A | T | - | - | - | - | - | - | - | - | - | - | 531 |
| YEAST | V | F | F | A | V | A | F | Y | Y | T | I | - | - | - | - | - | - | - | - | - | - | 457 |

| | | | | | | | | 590 | | | | | | | 600 | | |
|---|---|---|---|---|---|---|---|---|---|---|---|---|---|---|---|---|---|
| B. NAPUS 111 | L | R | V | W | H | S | L | R | L | L | D | L | S | L | K | M | L | V | P | H | 490 |
| B. NAPUS 411 | L | G | I | W | H | S | L | R | L | F | - | - | - | - | - | - | - | - | 480 |
| ARABIDOPSIS | R | R | F | W | H | S | L | R | I | L | A | W | A | L | Q | M | L | G | A | H | 488 |
| MOUSE | - | - | - | - | - | - | Y | F | C | F | K | S | E | P | W | A | T | K | P | R | A | 544 |
| RAT | - | - | - | - | - | - | Y | F | C | F | K | S | E | P | W | A | T | K | P | R | A | 545 |
| YEAST | - | - | - | - | - | - | Y | L | N | M | E | E | R | G | F | L | G | L | P | M | A | 471 |

| | | | | | | | | 610 | | | | | | | 620 | | |
|---|---|---|---|---|---|---|---|---|---|---|---|---|---|---|---|---|---|
| B. NAPUS 111 | L | K | A | E | G | I | G | Q | M | L | S | P | T | N | A | A | A | Y | R | K | 510 |
| B. NAPUS 411 | - | - | - | - | G | V | S | Q | M | L | S | P | A | Y | A | A | A | Y | R | K | 495 |
| ARABIDOPSIS | L | V | D | E | G | F | K | E | M | L | I | P | T | N | A | A | A | Y | R | R | 508 |
| MOUSE | L | F | S | S | G | A | V | L | Y | K | A | C | S | I | L | F | P | L | I | Y | 564 |
| RAT | L | F | S | S | G | A | I | L | Y | K | A | A | C | S | I | V | I | F | P | L | I | Y | 565 |
| YEAST | L | L | E | G | I | M | L | L | I | T | A | I | R | V | F | T | P | F | L | F | 491 |

| | | | | | | | |
|---|---|---|---|---|---|---|---|---|
| B. NAPUS 111 | S | Y | M | A | A | T | V | V | - | 519 |
| B. NAPUS 411 | S | Y | M | T | A | T | A | L | - | 504 |
| ARABIDOPSIS | N | Y | I | A | T | T | T | V | - | 517 |
| MOUSE | S | E | M | K | Y | L | V | H | - | 573 |
| RAT | S | E | M | K | Y | L | V | H | - | 574 |
| YEAST | G | E | - | - | - | L | I | G | - | 497 |

FIG. 1E

DNA SEQUENCES FROM BRASSICACEAE ENCODING SQUALENE EPOXIDASE AND PROCESS OF RAISING SQUALENE LEVELS IN PLANTS THEREWITH

CROSS-REFERENCE TO RELATED APPLICATIONS

This application is a National stage application of International Patent Application No. PCT/CA97/00175, filed Mar. 13, 1997, which claims benefit under 119(e) from Provisional Application No. 60/013,340 filed Mar. 13, 1996.

BACKGROUND OF THE INVENTION

1. Field of the Invention

This invention relates to the production of squalene for commercial and industrial uses. More particularly, the invention relates to a process by which natural squalene levels in plants can be increased, and to nucleotide sequences that can be introduced into plants to cause the desired increase, and plasmids, vectors, etc., useful in the process.

2. Description of the Related Art

There is a U.S. $125 million per annum market for squalene, a colourless oil used in the cosmetics and health industries (Kaiya, 1990). Squalene is currently obtained mainly from shark liver, but it also occurs in small quantities in vegetable oils. Squalene extracted from shark liver is declining in supply (Kaiya 1990) and the harvesting of sharks for this purpose is anyway environmentally unfriendly and is becoming less acceptable as environmental concerns increase in society.

Squalene can be extracted from olive oil, although the amounts are not sufficient to supply even the cosmetics market (Bondioli et al. 1992; Bondioli et al. 1993). Squalene could be extracted from other vegetable oils, but the levels of the hydrocarbon in the oil are too low for this to be economically viable. There are at present no Canadian crops used for squalene production. It has been suggested that, if the levels of squalene occurring in oilseeds could be increased, the traditional source of squalene could be replaced by oilseed crops, to the benefit of both the environment and those countries, such as Canada, that grow crops of this kind in abundance. Many vegetable oils undergo deodorization by vacuum distillation as a routine part of refining. Most of the squalene in the oil can be recovered in the deodorizer distillate which is a by-product of this process (Bondioli et al., 1993). Typically, squalene is concentrated more than one hundred fold in the deodorizer distillate relative to the levels in unrefined vegetable oils. For commercial viability, vegetable oil deodorizer distillates should contain at least 5% (w/w) squalene. Currently, soybean and canola deodorizer distillates contain squalene in the 0.1–3% range (Ramamurthi, S., 1994). Consequently, an increase of two-fold or more in the squalene content of these oilseeds could result in commercially viable squalene production from vegetable oils.

It has been shown that in plant cell cultures, squalene accumulates in the presence of squalene epoxidase inhibitors, e.g. allylamines such as terbinafine (Yates et al. 1991). Apparently, much of the squalene produced in plants is converted to the epoxide by squalene epoxidase, and ultimately to plant sterols. In fact, all plant and higher life forms contain squalene and squalene epoxidase genes, but little squalene accumulates in the tissues of such life forms because of the effects of the expressed squalene epoxidase. Therefore, inhibition of the epoxidase gives squalene an opportunity to accumulate. However, there are as yet no commercial processes based on this concept.

A main problem addressed by the inventors of the present invention is therefore to create a plant crop, particularly an oilseed crop, which accumulates squalene in harvestable tissues, such as seeds, at sufficient levels for commercially-viable extraction.

BRIEF SUMMARY OF THE INVENTION

An object of the present invention is to provide new sources of squalene that have the potential to be exploited on a commercial basis to replace conventional commercial sources of squalene.

Another object of the present invention, is to generate squalene-producing plants modified to accumulate squalene in the plant tissue (e.g. in seeds) in sufficient quantities to make the extraction of squalene commercially attractive.

Another object of the invention is to identify squalene epoxidase genes in plants, and to partially or completely neutralise the expression of such genes.

Another object of the invention is to produce DNA clones, constructs and vectors suitable for modifying the genomes of plants to reduce expression of squalene epoxidase.

Yet another object of the invention is to provide a commercial process for producing squalene from plant tissue, especially seeds.

The inventors of the present invention have discovered the DNA sequences of the genes encoding squalene epoxidase (squalene monooxygenase (2,3-epoxidizing); EC 1.14.99.7) from the plants *Arabidopsis thaliana* (thale cress), and *Brassica napus* (rapeseed, canola), as well as a second gene from Arabidopsis and one from *Ricinus communis* (castor), and using this knowledge have developed a process of modifying the genomes of such plants to produce genetically-modified plants which accumulate squalene at higher than natural levels. Moreover, the process may be operated to increase squalene levels in plants using DNA based on squalene epoxidase genes from different but related plants.

According to one aspect of the invention, there is provided an isolated and cloned DNA (polynucleotide) suitable for introduction into a genome of a plant to suppress expression of squalene epoxidase by said plant below natural levels, wherein the DNA has a sequence corresponding at least in part to a squalene epoxidase gene of a plant.

The DNA preferably has a sequence corresponding to all or part of a specific sequence selected from SEQ ID NO:1, SEQ ID NO:3, SEQ ID NO:5, SEQ ID NO:9 and SEQ ID NO:10 (as shown in the following Sequence Listing); or having at least 60% (more preferably at least 700%) homology thereto.

The measure of homology between two DNA (polynucleotide) sequences as used in this specification is the similarity index given by application of the Wilbur-Lipman algorithm of the MEGALIGN® computer program (DNASTAR) in aligning and comparing DNA sequences corresponding to a complete polypeptide coding region using the parameters ktuple=3, gap penalty=3 and window=20.

According to another aspect of the invention, there is provided a process of producing genetically-modified plants having increased levels of squalene in tissues of the plants compared to corresponding wild-type plants, wherein the plant genome is modified to suppress expression of squalene expoxidase by said plant. The genome is modified by introducing at least one exogenous DNA sequence that corresponds, at least in part, to one or more endogenous squalene epoxidase genes of the plant.

The DNA sequence introduced into said plant genome has at least 60%, and more preferably at least 70%, homology to said one or more of the endogenous squalene epoxidase genes, and is preferably all or part of a sequence selected from SEQ ID NO:1, SEQ ID NO:3, SEQ ID NO:5, SEQ ID NO:9 and SEQ ID NO:10.

According to yet another aspect of the invention, at least in a preferred form, there is provided a process of producing genetically-modified plants having increased levels of squalene in tissues of the plants compared to corresponding wild-type plants, wherein the plant genome is modified to suppress expression of squalene expoxidase by said plant, raising squalene levels of a plant, by introducing into the genome of the plant a nucleotide sequence that reduces or prevents expression of squalene epoxidase. The DNA introduced into the genome includes a transcriptional promoter and a sequence that when transcribed from the promoter is complementary or antisense to all or part of at least one squalene epoxidase messenger RNA produced by the plant.

The invention also relates to plasmids and vectors used in the processes indicated above, and as disclosed later.

The invention further relates to a genetically-modified plant capable of accumulating squalene at levels higher than the corresponding wild-type plant, produced by a process as indicated above, or a seed of such a plant.

The invention additionally relates to a process of producing squalene, which involves growing a genetically-modified plant as defined above, harvesting the plant or seeds of the plant, and extracting squalene from the harvested plant or seeds.

BRIEF DESCRIPTION OF THE SEVERAL VIEWS OF THE DRAWINGS

FIGS. 1A–1E show the alignment of deduced amino acid sequences of the clones pDR111 (*B. napus* 111) [SEQ ID NO:4], pDR411 (*B. napus* 411) [SEQ ID NO:11] and 129F12T7 (Arabidopsis) [SEQ ID NO:2], and of the known squalene epoxidase genes of mouse (DNA Database of Japan D42048) [SEQ ID NO:6], rat (DNA Database of Japan D37920) [SEQ ID NO:7], and baker's yeast (Genbank M64994) [SEQ ID NO:8]; the alignment was done using the MEGALIGN™ program of the LASERGENE™ suite of programs (DNASTAR) using a multiple alignment gap penalty of 20.

DETAILED DESCRIPTION OF THE INVENTION

General Discussion

Figure 2:
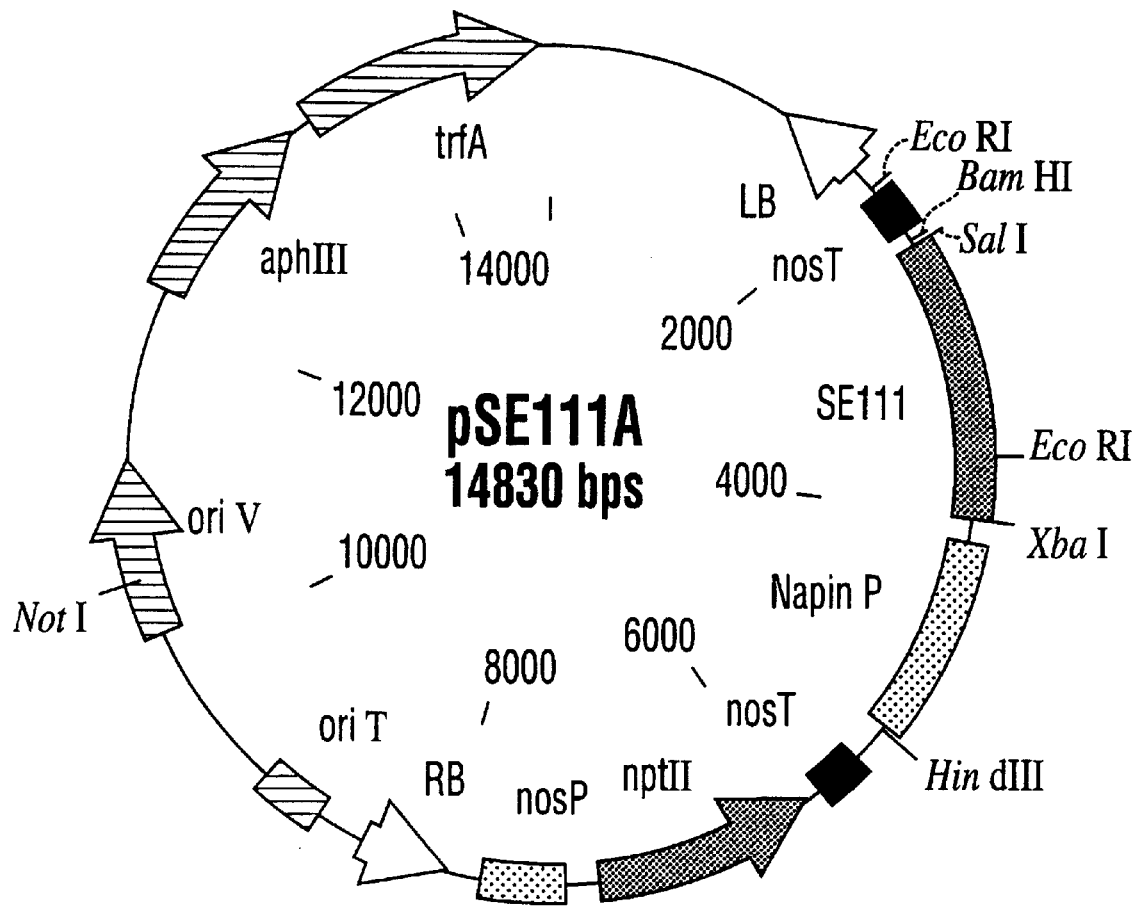
FIGS. 2, 3 and 4 are plasmid maps of three vectors (pSE111A, pSE411A and pSE129A, respectively) produced according to one embodiment of the present invention.

The concept underlying the present invention is to identify squalene epoxidase genes of oilseed plants (or possibly other plants, since all plants appear to have genes for the production of squalene, and particularly those plants that are capable of accumulating squalene in their harvestable tissue) and then to use that knowledge to create genetically-modified plants in which the expression of squalene expoxidase is decreased partially or fully compared to the natural level of expression, so that squalene naturally produced by the plants can accumulate in the seeds or other tissue to levels that make extraction commercially attractive.

The approach taken by the inventors of the present invention to identify squalene epoxidase genes of plants was initially to use the DNA sequence of a known squalene epoxidase gene from yeast to identify equivalent genes in suitable plant species, e.g. by heterologous hybridization, on the assumption that all squalene epoxidase genes will have a considerable degree of similarity. Once one or several plant squalene epoxidase genes have been identified in this way, those plant genes can then be used to identify additional squalene epoxidase genes from other plants.

Heterologous Hybridization

Nucleic acid hybridization is a technique used to identify specific nucleic acids from a mixture. Southern analysis is a type of nucleic acid hybridization in which DNA is typically digested with restriction enzymes, separated by gel electrophoresis and bound to a nitrocellulose or nylon membrane. A nucleic acid probe, which is typically radio-labeled or otherwise rendered easily detectable, is hybridized to the bound DNA by exposing it to the membrane-bound DNA under specific conditions and washing any unbound or loosely bound probe away. The location of the bound probe is then detected by autoradiography or other detection method. The location of the bound probe is an indication that DNA sequences that are similar to those in the probe nucleic acid are present. Hybridization may also be done with DNA of clones of a recombinant DNA library, such as a cDNA library, when that DNA has been bound to a membrane after plating the library out (Ausubel et al., 1994). Of course, the method used by the inventors to identify the genes disclosed in the present application may be used to identify equivalent genes from other plants. As noted above, the process originally used by the inventors to identify the Arabidopsis gene was based on further analysis of a gene that was tentatively identified from a publicly available database containing partial sequences (Expressed Sequence Tags or EST's) submitted by other workers from randomly chosen (unidentified) gene clones. EST's from other species (such as rice, castor) can also be searched in the same way to find other possible squalene epoxidase genes present in such plants (depending on the more or less accidental sequencing of the desired genes) using the Arabidopsis and *B. napus* sequences disclosed herein.

The inventors have, for example, found other EST's from plants that have tentatively been identified as squalene epoxidase genes by comparing them to the Ababidopsis and *B. napus* sequences discussed above. Thus, sequences corresponding to Genbank Accession Numbers T15019 (obtainable from Dr. C. R. Somerville, Carnegie Institution, 290 Panama St., Stanford, Calif. 94305, USA) and W43353 (obtainable from DNA Stock Center, Arabidopsis Biological Resource Center, Ohio State University, 1060 Carmack Road, Columbus, Ohio 43210-1002, USA) have been predicted to correspond to squalene epoxidases genes from *Ricinus communis* (castor) and Arabidopsis (a second Arabidopsis gene).

Perhaps more importantly, the process by which the *B. napus* gene was cloned can be used to clone other plant species. The (heterologous hybridization) methods are well known, but the process requires the knowledge and use of the novel plant squalene epoxidase sequences disclosed in this application.

If the hybridization and washing are done under conditions which are considered stringent (e.g., at relatively high temperature and/or low salt and/or high formamide concentration), then the sequences detected generally have a high degree of similarity to the probe nucleic acid. If hybridization and washing are done at lower stringency, then it is possible to detect sequences that are lower in similarity to the probe. Discussions of this detection of similar sequences by hybridization can be found in Beltz et al. (1983) and Yamamoto and Kadowaki (1995). From the point of view of gene cloning, if one obtains a clone for a gene in one organism, one can use low stringency hybridization of the DNA clones corresponding to a related organism to detect the homologous gene sequences of that organism. As mentioned before, the success of this approach depends on the similarity of the sequences of the homologous genes which in turn generally depends on the evolutionary relationship between the organisms.

Once identified, sequenced and cloned, the DNA of suitable plant species may then be modified or manipulated with any technique capable of decreasing the expression of a natural gene based on an isolated DNA clone corresponding, at least in part, to that gene. Suitable methods, at present, include antisense technologies (Bourque, 1995), co-suppression or gene silencing technologies (Meyer, 1995; Stam et al., 1997; Matzke and Matzke, 1995), and ribozyme technologies (Wegener et al. 1994; Barinaga, 1993).

These technologies are discussed in more detail below.

Down-regulation of Gene Expression

General

The activity of a particular enzyme, such as squalene epoxidase, is dependent on, among other things (such as the biochemical environment), the amount of enzyme (usually, and for the sake of this argument, a protein) that is present. The amount of enzyme present depends on the expression of the gene or genes encoding the enzyme of interest. Gene expression usually includes (not necessarily in this order) transcription of DNA to generate RNA, processing of the RNA produced from transcription, transport of RNA to the site of translation, translation of mature messenger RNA into polypeptide, proteolytic processing and folding of the nascent polypeptide, transport of the protein product to various cellular compartments, and post-translational modification of the protein (such as phosphorylation or glycosylation). Any effect or difference in any of the processes involved in gene expression can have an effect on the level of expression of an enzyme encoded by a given gene or genes. Gene expression often varies with cell type, tissue type and developmental stage. Likewise, enzyme levels in different cells and tissues and at different developmental stages varies widely. (For plant nuclear genes, this is often the result of differential transcription.)

Gene expression can also be affected by the breakdown of the gene product, the enzyme, or any of the intermediates in gene expression, such as precursor RNA.

From a genetic engineering point of view, in principle, gene expression can be down-regulated by affecting almost any of the processes involved. For example, although the mechanism is not well established, antisense technology (as discussed below) decreases the amount of translatable messenger RNA (mRNA) in an organism.

A) Antisense Technology

An appropriate antisense technology is disclosed, for example, in U.S. Pat. No. 5,190,931 issued on Mar. 2, 1993 to Masayori Inouye. The disclosure of this patent is incorporated herein by reference. In short, this technology can be used to regulate or inhibit gene expression in a cell by incorporating into the genetic material of the cell a nucleic acid sequence which is transcribed to produce an mRNA which is complementary to and capable of binding to the mRNA produced by the genetic material of the cell. The introduced nucleic acid sequences include equivalents of the gene to be regulated, or parts thereof, oriented in antisense fashion relative to a transcriptional promoter. Thus, the squalene epoxidase sequence, or part thereof, is introduced into the genetic material of the cell as a construct positioned between a transcriptional promoter segment and a transcriptional termination segment. The mRNA produced when the antisense sequences are transcribed binds or hybridizes to the mRNA from the squalene epoxidase gene of interest and prevents translation to a corresponding protein. Therefore, the protein coded for by the gene is not produced, or is produced in smaller quantities than would otherwise be the case. By introducing a gene that has a sequence that is antisense to the natural squalene epoxidase gene in oilseed plants, the epoxidation of squalene can be inhibited or reduced so that squalene accumulates in the plant tissues, especially the seeds, which can then be harvested in the usual way and the squalene extracted using conventional techniques.

In terms of the process of antisense down-regulation of squalene epoxidase genes, for any plant species, it is generally necessary to use a gene from a closely related plant such that the genes are more than about 60%, and preferably about 70%, identical at the DNA level (Murphy, 1996). Thus, homologous (equivalent) genes from the same family of plants, would reasonably be expected to give an antisense effect on any member species of that family. For example, Arabidopsis genes have been found to have antisense effects in *B. napus* (Murphy, 1996).

The antisense DNA in expressible form may be introduced into plant cells by any suitable transformation technique, e.g. in planta transformation (such as wound inoculation or vacuum infiltration). Transformation may also be carried out by co-cultivation of cotyledonary petioles and hypocotyl explants (e.g. of *B. napus* and *B. carinata*) with *A. tumefaciens* bearing suitable constructs (Moloney et al. (1989) and DeBlock et al.(1989)).

It would, of course, be optimal to identify a natural squalene epoxidase gene for each plant species to be modified in order to ensure complete correspondence of the DNA used to modify the natural gene and the DNA of the natural gene itself. If a gene from one plant species has been cloned, there are methods available to clone the same gene from other plants. The reliability of these methods (heterologous hybridization methods) depends on the similarity of the DNA sequence of the genes. If the DNA sequences have at least 60% of their sequence identical, and more preferably at least 70%, then the methods are usually reliable. Sequence similarity depends mostly on evolutionary (ancestral) relationships between plants. Practically, this means that either of the two genes first cloned by the inventors (the Arabidopsis and *B. napus* genes) may be used to clone the same gene in any other dicotyledonous plant (dicot), including, but not limited to soybean, tobacco, amaranth, potato, cotton, flax, bean, and pea. It is also reasonable to assume that the Arabidopsis or *B. napus* genes could also be used to clone the same genes from monocotyledonous plants (monocots), such as wheat, corn and barley.

The antisense effect occurs when hybridization can occur between antisense RNA and native RNA under the conditions prevailing in the cell. This may occur when the antisense RNA (and corresponding cDNA) contains as few as 20 nucleotides. More preferably, however, there should be at least 100 nucleotides in the cDNA to guarantee the required effect, and of course any larger portion up to the entire cDNA may be employed. In short, therefore, for effective antisense technology, the DNA sequence introduced into the plant genome should preferably be at least 20 consecutive nucleotides corresponding the native squalene epoxidase gene, and more preferably between 100 and the full DNA sequence of the gene. The homology of the added sequence may be at least 60%, and more preferably at least 70%, of the native plant gene.

B) Ribozyme Technology

Another method for downregulating gene expression by affecting mRNA levels is ribozyme technology. Ribozymes are RNA molecules capable of catalyzing the cleavage of RNA and other nucleic acids. In nature, Tetrahymena pre-ribosomal RNA, some viroids, virusoids and satellites RNAs of plant viruses perform self-cleavage reactions. The cleavage site for some plant pathogenic RNAs consists of a consensus structure, called the "hammmerhead" motif. The cleavage occurs within this hammerhead 3' to a GUX triplet, where X can be C, U, or A. The nucleotide region directing the catalysis of the cleavage reaction can be separated from the region where the cleavage occurs and the recognition of the target RNA can be modified by changing the nucleotide sequence of the regions flanking the cleavage site. As a consequence, ribozymes can be designed to catalyze cleavage reactions on targeted sequences of separate RNA substrates. This provides a means of regulating gene expression, if the DNA sequence of the gene is known.

In order to genetically engineer the down-regulation of a particular gene in plants, a vector can be constructed for transformation that includes one or more units, each of which may include a transcriptional promoter and a sequence encoding a ribozyme designed to cleave RNA transcribed from the gene or genes of interest. An example of this in plants has been provided by Schreier and co-workers (Steinecke et al. 1992, Wegener et al. 1994) in which a ribozyme was designed against neomycin phosphotransferase mRNA. Separate DNA constructs encoding the ribozyme and the neomycin phosphotransferase (npt) gene were used to transform plants. In plants containing both constructs, a reduction neomycin phosphotransferase activity was observed relative to plants transformed with only the npt gene construct.

Ribozyme technology also appears to be successful in other eukaryotes, such as the fruit fly (Zhao and Pick, 1993).

C) Co-suppression or Homology-Dependent Gene Silencing

When attempts have been made to overexpress homologous genes in plants, often a small fraction of the resulting transgenic plants are found to have very low levels of expression of both the native gene and the introduced gene (transgene). This phenomenon has been called co-suppression or homology-dependent gene silencing (Stam et al. 1996, Matzke and Matzke 1995). The mechanism by which co-suppression occurs is very poorly understood. However, advantage can be taken of the phenomenon to down-regulate the expression of a gene of interest. This can be accomplished by transforming a plant with a DNA construct which contains a strong transcriptional promoter driving the sense transcription of a DNA sequence with high similarity to the gene of interest. For example, when the chalcone synthase gene was introduced into petunia in an attempt to overproduce chalcone synthase (which is involved in flower pigment biosynthesis), some transgenic plants showed pigment patterns and enzyme levels that indicated the suppression of chalcone synthase gene expression (Jorgensen 1990). Investigation of examples such as these has shown that the effect is often associated with repetition of the transgene inserts in the plant genome. Cosuppression may be dependent on the coding region of a gene or on the promoter and other non-coding regions.

Thus, the down-regulation of squalene epoxidase in plants may be engineered with the use of cDNA sequence that are disclosed herein, or with plant genomic sequences which may include the promoter or promoters of squalene epoxidase genes.

D) Other Variations

Variations on the process of increasing squalene in plants include the use of different promoter sequences which may give rise to increased squalene in other tissues and at various stages of development. For example, the use of the cauliflower mosaic virus 35S promoter is likely to have an effect in most plant tissues. Other seed-specific and tissue-specific promoter may also be used.

Also, other plant transformation methods may be used such as the particle gun technique (Christou 1993).

As well, other vectors, selectable markers, transcription terminators, etc., may be used (Guerineau and Mullineaux 1993).

It has already been observed that overexpression of a fragment of the hamster 3-hydroxymethyl-3-glutaryl CoA reductase (HMGR) gene in plants can elevate squalene levels in plants (Chappell et al. 1994). This is likely due to the fact that the level of HMGR limits the flow of carbon through the mevalonate/sterol pathway that includes squalene. It would be expected that a combination of elevated HMGR levels and down-regulated squalene epoxidase levels would have an effect on raising squalene levels that would be larger than the effect of either elevated HMGR alone or down-regulated squalene epoxidase alone.

EXAMPLES

Identification of the Squalene Epoxidase Gene

The DNA sequence of the squalene epoxidase gene of yeast was published by Jandrositz et al. (1991). Using the TBLASTN™ computer search program (Altschul et al. 1990) and the yeast squalene epoxidase (predicted) amino acid sequence, the sequence was used to search a database which included partial cDNA sequences called "the Non-Redundant database" maintained by the National Center for Biotechnology Information (NCBI) in the United States. This database is a non-redundant nucleotide database made up of:

pdb Brookhaven Protein Data Bank, April 1994 Release genbank Genbank® Release 87.0, Feb. 15, 1995 gbupdate Genbank® cumulative updates to genbank major release embl EMBL data library, Release 41.0, December 1994 emblu E MBL Data Library, cumulative updates to embl major release maintained by the National Center for Biotechnology Information (NCBI), National Library of Medicine, National Institute of Health, Bethesda, Md. 20894, U.S.A.).

The database included expressed sequence tags (ESTs), i.e. partial sequences of more-or-less randomly chosen cDNA clones. This search identified the *Arabidopsis thaliana* cDNA clone 129F12T7 (Genbank accession no. T44667) as a putative squalene epoxidase gene. This clone was the seventh highest scoring sequence in this search and the highest scoring plant sequence. The P(N) of $1.9 \times 10^{-5}$ was considered borderline significant. The single high-scoring pair (HSP) of subsequences found was a stretch of 46 nucleotides with 21 positions identical (45%). Searches with the T44667 sequence revealed that a large portion of the 46 nucleotide region (29 nucleotides) matches a sequence motif found in a variety of enzymes that bound adenine dinucleotides, such as flavin adenine dinucleotide (FAD; which at least some squalene epoxidases are known to use as a cofactor; see Wierenga et al. 1986). So, in fact, the search, done when only the partial DNA sequence (T44667) was available, suggested the possibility, but did not confirm that T44667 corresponded to a squalene epoxidase gene.

The 129F12T7 clone was obtained and its DNA sequenced completely by the inventors at the Plant Biotech Institute of the National Research Council of Canada at Saskatoon, Saskatchewan, Canada. The DNA sequence of the cDNA insert of p129F12T7 is shown in the Sequence Listing (see later) as SEQ ID NO:1. After the full sequence of the insert of p129F12T7 was obtained, the Non-Redundant Protein Database (NCBI) was searched using the BLAST™ software (Altschul et al. 1990) (NCBI) based on the predicted amino acid sequence. The amino acid sequence corresponding to the open reading frame of SEQ ID NO:1 are shown in the Sequence Listing as SEQ ID NO:2. The Arabidopsis sequence gave the highest scoring matches with squalene epoxidase sequences including that of rat (P(N)= $5 \times 10^{-60}$) and yeast (P(N)=$9.2 \times 10^{-33}$). No sequences which had been reliably identified had P(N) values less than $10^{-6}$. These numbers indicate that the product of the Arabidopsis gene is, in all probability, squalene epoxidase.

The 129F12T7 clone was used to probe a *B. napus* cDNA library, obtained from Dr. Edward Tsang of the Plant Biotech Institute. Two independent clones, pDR111 and pDR411 were isolated and sequenced. The Sequence Listing shows the DNA sequences of the cDNA inserts of pDR111 [SEQ ID NO:3] and pDR411 [SEQ ID NO:5] and the amino acid sequences corresponding to the coding regions of SEQ ID NO:3 [SEQ ID NO:4] and SEQ ID NO:5 [SEQ ID NO:11]. pDR111 and pDR411 have similar (but not identical) DNA sequences which are also similar to the 129F12T7 sequence. Plasmids p129F12T7, pDR111 and pDR411 were deposited at the American Type Culture Collection (ATCC), 10801 University Boulevard, Manassas, Va. 20110 USA, under the terms of the Budapest Treaty on Jan. 9, 1997 and were accepted. The deposit numbers are, respectively, ATCC 97847, ATCC 97846 and ATCC 97845. A single deposit receipt and statement of viability was issued for all three deposits on Jan. 17, 1997.

Figure 1B:
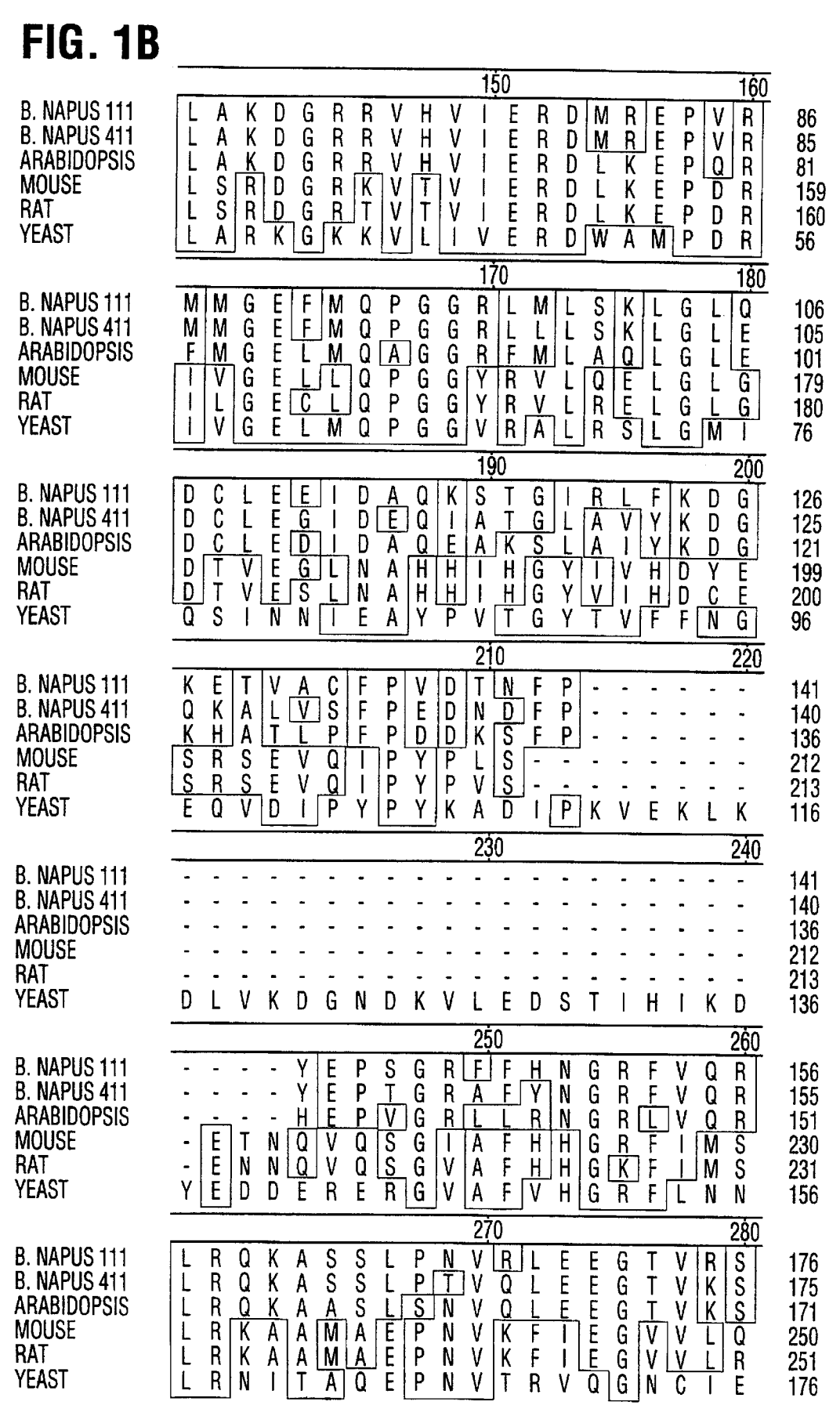

FIG. 1 of the accompanying drawings shows an alignment of amino acid sequences for the 129F12T7 clone [SEQ ID NO:2], the pDR111 clone [SEQ ID NO:4] and the pDR411 [SEQ ID NO:11] clone, along with the squalene epoxidase sequences amino acid sequences for mouse [SEQ ID NO:6], rat [SEQ ID NO:7] and yeast [SEQ ID NO:8]. The plant sequence show blocks of high similarity to the non-plant sequences, including the region thought to correspond to an adenine dinucleotide-binding site (residues 45–88 of the Arabidopsis sequence; Wierenga et al. 1986; Sakakibara et al. 1995), as well as in the C-terminal half of the sequence. The amino acid sequence similarities based on this alignment are shown in Table 1 below.

TABLE 1

Amino acid sequence similarities calculated by MEGALIGN ™ software for the sequence alignment of FIG. 1.

| | PDR411 Predicted Amino Acid Sequence | p129F12T7 Predicted Amino Acid Sequence | Mouse Squalene Epoxidase Predicted Amino Acid Sequence | Rat Squalene Epoxidase Predicted Amino Acid Sequence | Yeast Squalene Epoxidase Predicted Amino Acid Sequence |
|---|---|---|---|---|---|
| pDR111 Predicted Amino Acid Sequence | 74.8 | 59.6 | 27.0 | 26.4 | 21.5 |
| pDR411 Predicted Amino Acid Sequence | | 62.9 | 29.2 | 27.8 | 21.3 |
| p129F12T7 Predicted Amino Acid Sequence | | | 27.3 | 26.1 | 20.9 |
| Mouse Squalene Epoxidase Predicted Amino Acid Sequence | | | | 91.8 | 30.4 |
| Rat Squalene Epoxidase Predicted Amino Acid Sequence | | | | | 30.4 |

Analysis of the pDR411 sequence suggests it has an intron in the 3'-end of its amino acid coding region which is, of course, unusual in cDNA. If nucleotides 1473–1629 (inclusive) are removed from the sequence and the cDNA translated, the C-terminus is more similar to the pDR111 and p129F12T7 amino acid sequences [SEQ ID NO:4 and SEQ ID NO:2]. Also, there are sequence patterns in this region that are common to other plant introns (5' and 3' splice consensus sequences and high AT content (Goodall and Filipowicz, 1991)). This may mean that the pDR411 clone represents an intermediate or precursor RNA, rather than the final messenger RNA (mRNA). There can therefore be less certainty in predicting the full amino acid sequence corresponding to pDR411, although this predicted sequence is shown in FIG. 1 [SEQ ID NO:11]. However, the possible presence of a small intron in the 3'-end of pDR411 does not cause a problem for its use in antisense techniques.

Employing the plant squalene epoxidase sequences, transgenic plants can be generated which accumulate squalene in their seeds. This can be done by established genetic transformation methods using DNA constructs that include the napin or other seed-specific promoters (Kridl, 1988; Anonymous, 1995) and fragments of plant squalene epoxidase genes arranged in the antisense orientation. Downregulation of the squalene epoxidase gene in seeds by antisense technology (Inouye, 1990; Bourque, 1995) will prevent the conversion of squalene to squalene expoxide and result in squalene accumulation.

ISOLATION OF SQUALENE EPOXIDASE GENE IN *B. NAPUS*

The 129F12T7 clone obtained as described above was used to probe for the homologous gene in *B. napus* as follows.

Unless otherwise noted all molecular biology methods were performed as described in Ausubel et al.(1994).

The Arabidopsis 129F12T7 DNA Probe

The plasmid p129F12T7 was digested with the restriction enzymes Sal I and Not I. The resulting DNA fragments were separated by agarose gel electrophoresis.

The 1.8 kb Sal I/Not I DNA fragment corresponding to the Arabidopsis squalene epoxidase cDNA was purified from a gel band. A radiolabelled DNA probe was prepared by the random priming method and [alpha-32P]-dCTP (deoxycytidine triphosphate).

Library Screening

The probe produced as above was used to screen a *B. napus* cDNA library, kindly provided by Dr. Edward Tsang of the Plant Biotechnology Institute (Saskatoon, Saskatchewan, Canada). To construct the library, *B. napus* seedlings (cv. Westar) were grown (on half strength Murashige and Skoog agar (1%) medium supplemented with 1% sucrose) in the dark at 22° C. for two weeks after germination and exposed to light for 24 hours. PolyA+RNA was extracted from the seedlings and first strand cDNA synthesis was primed with an oligo dT/Not I adapter/primer. Sal I adapters were ligated after second strand cDNA synthesis and a library was constructed in Not I/Sal I arms of the LambdaZipLox vector (Life Technologies).

The library was plated using standard methods and the Y1090 strain of *E. coli*. Approximately 25,000 plaques from the library were plated, lifted onto Hybond®-C nylon membranes (Amersham) and hybridized with the above probe according to the manufacturer's instructions. After two rounds of plaque purification, two independent clones, pDR111 and pDR411 were isolated by in vivo excision.

The p129F12T7, pDR111 and pDR411 clones were sequenced using the PRISM® DyeDeoxy Terminator Cycle Sequencing System (Perkin Elmer/Applied Biosystems) and a Model 373 DNA Sequencer (Applied Biosystems). DNA sequences were assembled and analyzed using the Lasergene® suite of software (DNASTAR, Inc.) and BLAST® and related software of the NCBI.

CONSTRUCTION OF VECTORS FOR PLANT TRANSFORMATION

Figure 3:
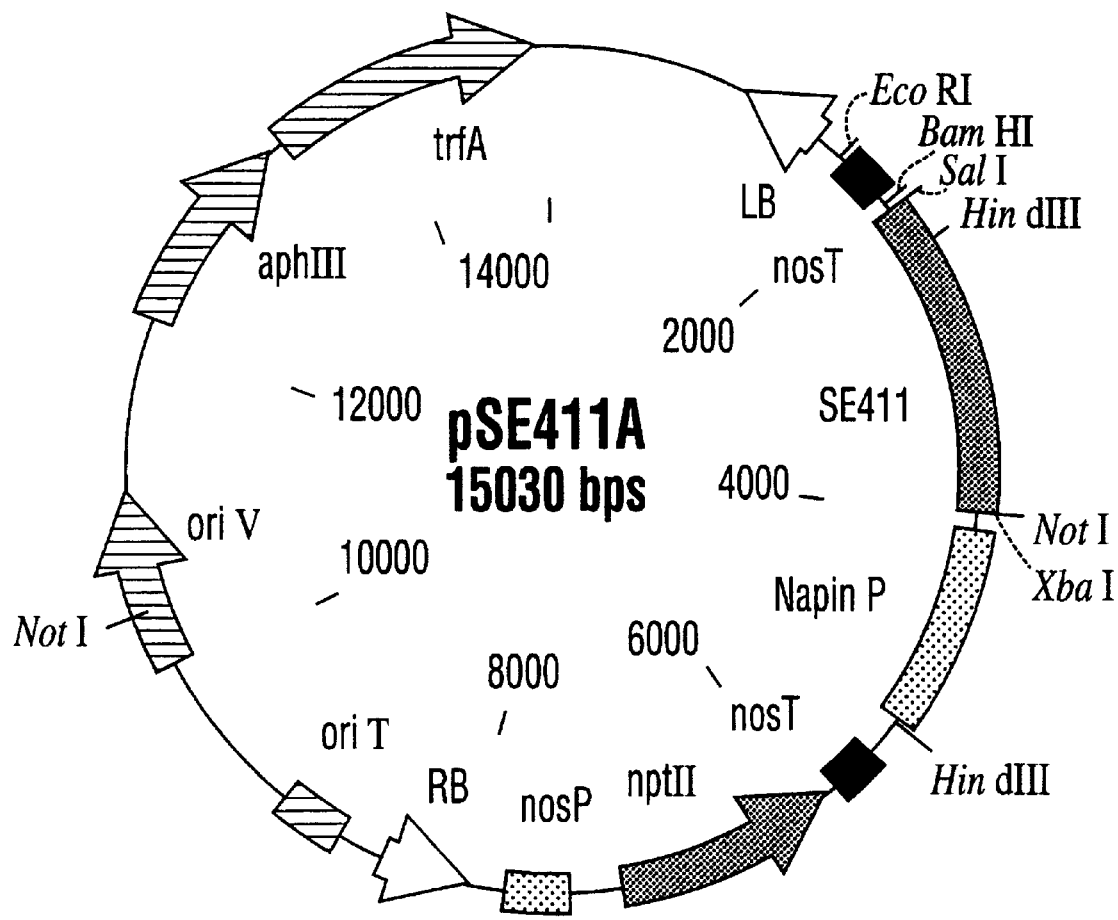
Figure 4:
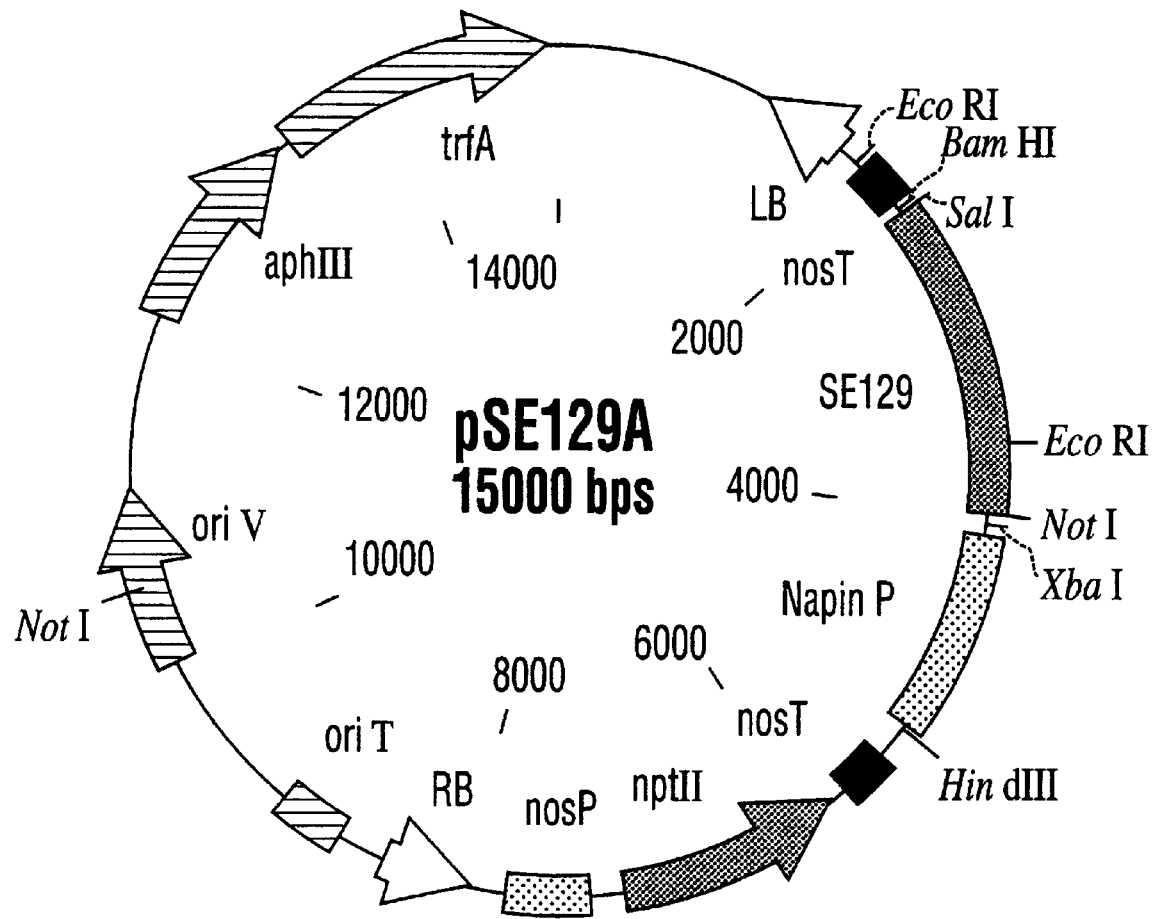

FIGS. 2, 3 and 4 show three vectors constructed for plant transformation, namely pSE129A, pSE111A and pSE411 A. In these drawings, the following abbreviations are used:

| | |
|---|---|
| nosT | 3'-terminus of the nopaline synthase gene |
| SE129 | Sal I/Not I insert of p129F12T7 |
| SE111 | Sal I/Xba I fragment of the insert of pDR111 |
| SE411 | Sal I/Not I insert of pDR411 |
| Napin P | napin gene promoter (Josefsson 1986). |

All other elements are described by Guerineau and Mullineaux (1993), Thomas et al. (1992) and Beban (1984).

These Plasmids Were Constructed as Follows pDH1

The plasmid pE35SNT was obtained from Raju Datla (Plant Biotechnology Institute, Saskatoon, Saskatchewan Canada). It contains a double 35S promoter and nopaline synthase (Nos) terminator (Datla, 1992) in pUC19. It was digested with Hind III and Xba I to remove the double 35S promoter. The napin promoter (Josefsson et al. 1987) was isolated from pNap (obtained from Ravi Jain, Plant Biotechnology Institute, Saskatoon, Saskatchewan, Canada) by Hind III and Xba I digestion. The plasmid pDH1 was produced by ligation of the large pE35SNT/Hind III/Xba I fragment and the Hind III/Xba I napin promoter fragment. Thus, pDH1 contained the napin promoter and the Nos terminator between the Hind III and EcoR I sites of the pUC19 vector.

pSE129A

The p129F12T7 plasmid was digested with Pst I and Hind III. The fragment containing the Arabidopsis squalene epoxidase cDNA was ligated to the Pst I- and Hind III-digested vector pTrcHisB (INVITROGEN®) to give the circular plasmid pTrcHis129. pTrcHis129 was digested with Xba I and BamH I and the squalene epoxidase cDNA fragment was ligated into Xba I- and BamH I-digested pDH1. The resulting plasmid pDH129A contained the squalene epoxidase cDNA in antisense orientation downstream from the napin promoter and upstream of the Nos terminator. pDH129A was digested with Hind III and partially digested EcoR I and the fragment containing napin promoter, squalene epoxidase cDNA and Nos terminator was ligated into Hind III- and EcoR I-digested pRD400 (a binary vector for plant transformation containing a gene conferring kanamycin resistance; (Datla et al. 1992)) to give pSE129A.

pSE111A

The pDR111 plasmid was digested with Sma I and Xba I. The fragment containing a *B. napus* squalene epoxidase cDNA (excluding a small part of the 3' end downstream of the Xba I site) was ligated to the large fragment of Sma I- and XBa I-digested pDH129 vector (containing the napin promoter and Nos terminator) to give the circular plasmid pDH111A. pDH111A contained the squalene epoxidase cDNA in antisense orientation downstream from the napin promoter and upstream of the Nos terminator. pDH111A was digested with Hind III and partially with EcoR I and the fragment containing napin promoter, cDNA and Nos terminator was ligated into Hind III- and EcoR I-digested pRD400 to give pSE111A.

pSE411A

The pDR411 plasmid was digested with Sma I and Xba I. The fragment containing a *B. napus* squalene epoxidase cDNA was ligated to the large fragment of Sma I- and Xba I-digested pDH129A vector (containing the napin promoter and Nos terminator and excluding the Arabidopsis cDNA sequence) to give the circular plasmid pDH411A. pDH411A contained the squalene epoxidase cDNA in antisense orientation downstream from the napin promoter and upstream of the Nos terminator. pDH111A was digested with EcoR I and partially digested with Hind III and the fragment containing napin promoter, squalene epoxidase cDNA and Nos terminator was ligated into Hind III- and EcoR I-digested pRD400 (Datla et al. 1992) to give pSE411A.

The final vectors pSE129A, pSE111A and pSE411A were deposited on Mar. 5, 1997 under the terms of the Budapest Treaty at the American Type Culture Collection, 10801 University Boulevard, Manassas, Va. 20110, USA; under deposit nos. ATCC 97910, ATCC 97909 and ATCC 97908, respectively). These vectors were introduced into *Agrobacterium tumefaciens* strain GV3101 (bearing helper plasmid pMP90; Koncz and Schell, 1986) by electroporation.

PLANT GROWTH CONDITIONS

All *A. thaliana* control and transgenic plants were grown in controlled growth chambers, under continuous fluorescent illumination (150–200 $\mu E$ $m^{-2}$ $sec^{-1}$) at 22° C., as described by Katavic et al.(1995).

PLANT TRANSFORMATION

The pSE129A construct was tested in *A. thaliana* by in planta transformation techniques.

Wild type (WT) *A. thaliana* plants of ecotype Columbia were grown in soil. In planta transformation was performed by vacuum infiltration (Bechtold et al. 1993) with overnight bacterial suspension of *A. tumefaciens* strain GV3101 bearing helper nopaline plasmid pMP90 (disarmed Ti plasmid with intact vir region acting in trans, gentamycin and kanamycin selection markers; Koncz and Schell (1986)) and binary vector pSE129A.

After infiltration, plants were grown to set seeds ($T_1$ generation). Dry seeds ($T_1$ generation of seeds) were harvested in bulk and screened on selective medium with 50 mg/L kanamycin. After two to three weeks on selective medium, surviving seedlings were transferred to soil. Mature seeds from these seedlings ($T_2$ seeds) were used for squalene analysis. Mature seeds from untransformed wild type (WT) Columbia plants and pRD400 transgenic plants (binary vector pRD400, containing only kanamycin selection marker; Datla et al. 1992) were used as controls in analyses of seed lipids.

Seed Analysis

Seeds were analyzed for squalene levels as follows:

In all steps, care was taken to avoid contamination from external sources, particularly human skin. 5–10 mg of Arabidopsis seeds were weighed and rinsed with hexane to remove any external contamination. 1 ml of 7.5% KOH (in 95% methanol) was added to each sample and 250 ng of squalane were added as internal standard. (Squalane is the hydrogenated form of squalene.) Seeds were homogenized with a Polytron® (Model PRO200, PRO Scientific) at maximum speed for 40 seconds. The head of the Polytron was washed with 1 ml of 7.5% KOH (in 95% methanol) and the wash was pooled with the homogenate. The mixture was incubated at 80° C. for 1 hr, then cooled to room temperature. The mixture was centrifuged at 3000 g for 5 min, and the supernatant was transferred to a fresh tube. One ml of $H_2O$ and 1.5 ml of hexane were added to the supernatant and, after vortexing, the mixture was centrifuged at 3000 g for 5 minutes. The hexane (top) layer was transferred to another test tube. The aqueous phase was re-extracted with 1.5 ml hexane and the hexane fractions were pooled. The hexane fraction was extracted with 1 ml of water/methanol/KOH (50:50:2) and evaporated under nitrogen. The residue was dissolved in 50 μl of hexane and transferred to an autosampler vial. Gas-liquid chromatography was performed with a DB5 column (J & W Scientific, USA) using the following parameters:

| Column Temperature: | 0–1 min | 180° C. |
|---|---|---|
| | 1–16 min | 180-280° C. (linear ramp) |
| | 16–30 min | 280° C. |
| Injector Temperature | | 275° C. |
| Detector Temperature | | 300° C. |

Transgenic Results

Seeds from 9 Arabidopsis lines transformed with pRD400 and 55 lines transformed with pSE129A were analyzed for squalene content. Table 2 below shows the results for all of the pRD400 transgenic lines and 4 pSE129A lines.

TABLE 2

| Line | Vector | Squalene ug/g dry weight | Standard Deviation of 3 Assays |
|---|---|---|---|
| k401 | pRD400 | 4.04 | 0.5 |
| k402 | pRD400 | 4.71 | 0.16 |
| k403 | pRD400 | 4.39 | 0.34 |
| k404 | pRD400 | 4.86 | 0.75 |
| k405 | pRD400 | 3.92 | 0.92 |
| k406 | pRD400 | 4.04 | 1.68 |
| k409 | pRD400 | 5.03 | 0.85 |
| k410 | pRD400 | 6.09 | 1.22 |
| k411 | pRD400 | 4.57 | 1.26 |
| k9 | pSE129A | 9.96 | 1.59 |
| k12 | pSE129A | 11.34 | 2.01 |
| k50 | pSE129A | 12.38 | 0.35 |
| k54 | pSE129A | 9.76 | 1.43 |

The mean and standard deviation of the 9 pRD400 lines is 4.6 and 0.7, respectively.

---

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 1756 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Arabidopsis thaliana
      (B) STRAIN: Columbia
      (D) DEVELOPMENTAL STAGE: 3 different stages
      (F) TISSUE TYPE: 4 different tissues

```
        (vii) IMMEDIATE SOURCE:
              (A) LIBRARY: Lambda-PRL2
              (B) CLONE: 129F12T7

(ix) FEATURE:
              (A) NAME/KEY: CDS
              (B) LOCATION:15..1565
              (D) OTHER INFORMATION:/codon_start= 15
                  /function= "converts squalene to
                  2,3-oxidosqualene"
                  /EC_number= 1.14.99.7
                  /product= "squalene epoxidase"
                  /standard_name= "squalene monooxygenase
                  (2,3-epoxidizing)"

(ix) FEATURE:
              (A) NAME/KEY: 3'UTR
              (B) LOCATION:1566..1756

(ix) FEATURE:
              (A) NAME/KEY: polyA_site
              (B) LOCATION:1756

(ix) FEATURE:
              (A) NAME/KEY: 5'UTR
              (B) LOCATION:1..14

(xi) SEQUENCE DESCRIPTION: SEQ ID NO: 1:

CCACGCGTCC GGCA ATG ACT TAC GCG TGG TTA TGG ACG CTT CTC GCC TTT         50
              Met Thr Tyr Ala Trp Leu Trp Thr Leu Leu Ala Phe
                1               5                  10

GTT CTG ACA TGG ATG GTT TTT CAC CTC ATC AAG ATG AAG AAG GCG GCA         98
Val Leu Thr Trp Met Val Phe His Leu Ile Lys Met Lys Lys Ala Ala
             15                  20                  25

ACC GGA GAT TTA GAG GCC GAG GCA GAA GCA AGA AGA GAT GGT GCA ACG        146
Thr Gly Asp Leu Glu Ala Glu Ala Glu Ala Arg Arg Asp Gly Ala Thr
 30                  35                  40

GAT GTC ATC ATT GTT GGG GCG GGT GTT GCA GGC GCT TCT CTT GCT TAT        194
Asp Val Ile Ile Val Gly Ala Gly Val Ala Gly Ala Ser Leu Ala Tyr
 45                  50                  55                  60

GCT TTA GCT AAG GAT GGA CGA CGA GTA CAT GTG ATA GAG AGG GAC TTA        242
Ala Leu Ala Lys Asp Gly Arg Arg Val His Val Ile Glu Arg Asp Leu
                 65                  70                  75

AAA GAG CCA CAA AGA TTC ATG GGA GAG CTG ATG CAA GCG GGA GGT CGC        290
Lys Glu Pro Gln Arg Phe Met Gly Glu Leu Met Gln Ala Gly Gly Arg
             80                  85                  90

TTC ATG TTA GCC CAG CTT GGC CTC GAA GAT TGT TTG GAG GAC ATA GAC        338
Phe Met Leu Ala Gln Leu Gly Leu Glu Asp Cys Leu Glu Asp Ile Asp
             95                 100                 105

GCA CAA GAA GCG AAG TCC TTG GCA ATA TAC AAG GAT GGA AAA CAC GCG        386
Ala Gln Glu Ala Lys Ser Leu Ala Ile Tyr Lys Asp Gly Lys His Ala
110                 115                 120

ACA TTG CCT TTT CCA GAT GAC AAG AGT TTT CCT CAT GAG CCA GTA GGT        434
Thr Leu Pro Phe Pro Asp Asp Lys Ser Phe Pro His Glu Pro Val Gly
125                 130                 135                 140

AGA CTC TTA CGT AAT GGT CGG CTG GTA CAA CGT TTA CGC CAA AAA GCA        482
Arg Leu Leu Arg Asn Gly Arg Leu Val Gln Arg Leu Arg Gln Lys Ala
                145                 150                 155

GCT TCT CTT AGC AAT GTT CAA TTA GAA GAA GGA ACA GTG AAG TCT TTA        530
Ala Ser Leu Ser Asn Val Gln Leu Glu Glu Gly Thr Val Lys Ser Leu
                160                 165                 170

ATT GAA GAA GAA GGA GTG GTC AAA GGA GTG ACA TAC AAA AAT AGC GCA        578
Ile Glu Glu Glu Gly Val Val Lys Gly Val Thr Tyr Lys Asn Ser Ala
                175                 180                 185

GGC GAA GAA ATA ACG GCC TTT GCA CCT CTT ACT GTC GTA TGC GAT GGT        626
```

```
Gly Glu Glu Ile Thr Ala Phe Ala Pro Leu Thr Val Val Cys Asp Gly
    190                 195                 200

TGT TAT TCG AAC CTT CGT CGG TCA CTC GTG GAT AAT ACT GAG GAA GTC        674
Cys Tyr Ser Asn Leu Arg Arg Ser Leu Val Asp Asn Thr Glu Glu Val
205             210                 215                 220

CTC TCG TAC ATG GTG GGT TAC GTC ACG AAG AAT AGC CGA CTT GAA GAT        722
Leu Ser Tyr Met Val Gly Tyr Val Thr Lys Asn Ser Arg Leu Glu Asp
                225                 230                 235

CCC CAT AGT CTA CAT TTG ATA TTT TCT AAA CCT TTG GTT TGT GTT ATA        770
Pro His Ser Leu His Leu Ile Phe Ser Lys Pro Leu Val Cys Val Ile
            240                 245                 250

TAT CAA ATA ACC AGT GAT GAA GTT CGT TGT GTT GCC GAA GTT CCC GCT        818
Tyr Gln Ile Thr Ser Asp Glu Val Arg Cys Val Ala Glu Val Pro Ala
            255                 260                 265

GAT AGT ATT CCT TCT ATA TCG AAT GGT GAA ATG TCT ACC TTC CTC AAG        866
Asp Ser Ile Pro Ser Ile Ser Asn Gly Glu Met Ser Thr Phe Leu Lys
270                 275                 280

AAA TCA ATG GCT CCT CAG ATA CCT GAA ACT GGA AAT CTT CGG GAG ATA        914
Lys Ser Met Ala Pro Gln Ile Pro Glu Thr Gly Asn Leu Arg Glu Ile
285                 290                 295                 300

TTT TTG AAA GGC ATA GAG GAA GGA TTA CCA GAG ATA AAA TCA ACA GCG        962
Phe Leu Lys Gly Ile Glu Glu Gly Leu Pro Glu Ile Lys Ser Thr Ala
                305                 310                 315

ACG AAA AGT ATG TCA TCG AGA TTG TGT GAT AAA AGA GGA GTG ATT GTG       1010
Thr Lys Ser Met Ser Ser Arg Leu Cys Asp Lys Arg Gly Val Ile Val
                320                 325                 330

TTG GGA GAT GCA TTC AAT ATG CGT CAT CCT ATA ATC GCG TCA GGA ATG       1058
Leu Gly Asp Ala Phe Asn Met Arg His Pro Ile Ile Ala Ser Gly Met
            335                 340                 345

ATG GTT GCA CTC TCG GAC ATT TGC ATT CTA CGC AAT CTT CTC AAA CCA       1106
Met Val Ala Leu Ser Asp Ile Cys Ile Leu Arg Asn Leu Leu Lys Pro
            350                 355                 360

TTG CCT AAC CTC AGC AAT ACT AAG AAA GTC TCT GAT CTT GTC AAG TCC       1154
Leu Pro Asn Leu Ser Asn Thr Lys Lys Val Ser Asp Leu Val Lys Ser
365                 370                 375                 380

TTT TAC ATC ATC CGC AAG CCA ATG TCA GCG ACC GTG AAC ACG CTC GCG       1202
Phe Tyr Ile Ile Arg Lys Pro Met Ser Ala Thr Val Asn Thr Leu Ala
                385                 390                 395

AGT ATC TTT TCA CAA GTG CTT GTT GCT ACA ACA GAC GAA GCA AGA GAG       1250
Ser Ile Phe Ser Gln Val Leu Val Ala Thr Thr Asp Glu Ala Arg Glu
            400                 405                 410

GGA ATG CGA CAA GGC TGC TTC AAT TAC CTA GCT CGT GGA GAT TTT AAA       1298
Gly Met Arg Gln Gly Cys Phe Asn Tyr Leu Ala Arg Gly Asp Phe Lys
            415                 420                 425

ACA AGG GGA TTG ATG ACT ATT CTC GGA GGC ATG AAC CCT CAC CCT CTT       1346
Thr Arg Gly Leu Met Thr Ile Leu Gly Gly Met Asn Pro His Pro Leu
        430                 435                 440

ACT CTA GTC CTT CAT CTT GTA GCC ATC ACC CTT ACG TCC ATG GGC CAC       1394
Thr Leu Val Leu His Leu Val Ala Ile Thr Leu Thr Ser Met Gly His
445                 450                 455                 460

TTG CTC TCT CCG TTT CCT TCG CCT CGT CGC TTT TGG CAT AGC CTC AGA       1442
Leu Leu Ser Pro Phe Pro Ser Pro Arg Arg Phe Trp His Ser Leu Arg
                465                 470                 475

ATT CTT GCC TGG GCT TTG CAA ATG TTG GGT GCA CAT TTA GTG GAT GAA       1490
Ile Leu Ala Trp Ala Leu Gln Met Leu Gly Ala His Leu Val Asp Glu
            480                 485                 490

GGA TTC AAG GAA ATG TTG ATT CCA ACA AAC GCA GCT GCT TAT CGA AGG       1538
Gly Phe Lys Glu Met Leu Ile Pro Thr Asn Ala Ala Ala Tyr Arg Arg
            495                 500                 505
```

```
AAC TAT ATC GCC ACA ACC ACT GTT TGA TCAATCCATA ACACGAAGAC                    1585
Asn Tyr Ile Ala Thr Thr Thr Val
    510                 515

TGTTTTATTC GGAGATGAAA AATAACAACT CAAACAGTTA ACTTTCTACA ACCAAATAAA            1645

TAATTGTGTG TATATGAAGT TGAGCCTATG GTTAAGCTCT ACTGAATTGT GTTGAAAACA            1705

AACATGGATA TGTTATATGC TAATTTGTTA TATTCTATTT ATTGATTCTT G                    1756

(2) INFORMATION FOR SEQ ID NO: 2:

(i) SEQUENCE CHARACTERISTICS:
        (A) LENGTH: 516 amino acids
        (B) TYPE: amino acid
        (D) TOPOLOGY: linear (ii) MOLECULE TYPE: protein (xi) SEQUENCE DESCRIPTION: SEQ ID NO: 2:
```

Met Thr Tyr Ala Trp Leu Trp Thr Leu Leu Ala Phe Val Leu Thr Trp
 1               5                  10                  15

Met Val Phe His Leu Ile Lys Met Lys Lys Ala Ala Thr Gly Asp Leu
                20                  25                  30

Glu Ala Glu Ala Glu Ala Arg Arg Asp Gly Ala Thr Asp Val Ile Ile
            35                  40                  45

Val Gly Ala Gly Val Ala Gly Ala Ser Leu Ala Tyr Ala Leu Ala Lys
        50                  55                  60

Asp Gly Arg Arg Val His Val Ile Glu Arg Asp Leu Lys Glu Pro Gln
 65                 70                  75                  80

Arg Phe Met Gly Glu Leu Met Gln Ala Gly Arg Phe Met Leu Ala
                85                  90                  95

Gln Leu Gly Leu Glu Asp Cys Leu Glu Asp Ile Asp Ala Gln Glu Ala
               100                 105                 110

Lys Ser Leu Ala Ile Tyr Lys Asp Gly Lys His Ala Thr Leu Pro Phe
           115                 120                 125

Pro Asp Asp Lys Ser Phe Pro His Glu Pro Val Gly Arg Leu Leu Arg
       130                 135                 140

Asn Gly Arg Leu Val Gln Arg Leu Arg Gln Lys Ala Ala Ser Leu Ser
145                 150                 155                 160

Asn Val Gln Leu Glu Glu Gly Thr Val Lys Ser Leu Ile Glu Glu Glu
               165                 170                 175

Gly Val Val Lys Gly Val Thr Tyr Lys Asn Ser Ala Gly Glu Glu Ile
               180                 185                 190

Thr Ala Phe Ala Pro Leu Thr Val Val Cys Asp Gly Cys Tyr Ser Asn
           195                 200                 205

Leu Arg Arg Ser Leu Val Asp Asn Thr Glu Glu Val Leu Ser Tyr Met
       210                 215                 220

Val Gly Tyr Val Thr Lys Asn Ser Arg Leu Glu Asp Pro His Ser Leu
225                 230                 235                 240

His Leu Ile Phe Ser Lys Pro Leu Val Cys Val Ile Tyr Gln Ile Thr
               245                 250                 255

Ser Asp Glu Val Arg Cys Val Ala Glu Val Pro Ala Asp Ser Ile Pro
           260                 265                 270

Ser Ile Ser Asn Gly Glu Met Ser Thr Phe Leu Lys Lys Ser Met Ala
       275                 280                 285

Pro Gln Ile Pro Glu Thr Gly Asn Leu Arg Glu Ile Phe Leu Lys Gly
       290                 295                 300

```
Ile Glu Glu Gly Leu Pro Glu Ile Lys Ser Thr Ala Thr Lys Ser Met
305                 310                 315                 320

Ser Ser Arg Leu Cys Asp Lys Arg Gly Val Ile Val Leu Gly Asp Ala
            325                 330                 335

Phe Asn Met Arg His Pro Ile Ile Ala Ser Gly Met Met Val Ala Leu
            340                 345                 350

Ser Asp Ile Cys Ile Leu Arg Asn Leu Leu Lys Pro Leu Pro Asn Leu
        355                 360                 365

Ser Asn Thr Lys Lys Val Ser Asp Leu Val Lys Ser Phe Tyr Ile Ile
    370                 375                 380

Arg Lys Pro Met Ser Ala Thr Val Asn Thr Leu Ala Ser Ile Phe Ser
385                 390                 395                 400

Gln Val Leu Val Ala Thr Thr Asp Glu Ala Arg Glu Gly Met Arg Gln
                405                 410                 415

Gly Cys Phe Asn Tyr Leu Ala Arg Gly Asp Phe Lys Thr Arg Gly Leu
            420                 425                 430

Met Thr Ile Leu Gly Gly Met Asn Pro His Pro Leu Thr Leu Val Leu
        435                 440                 445

His Leu Val Ala Ile Thr Leu Thr Ser Met Gly His Leu Leu Ser Pro
    450                 455                 460

Phe Pro Ser Pro Arg Arg Phe Trp His Ser Leu Arg Ile Leu Ala Trp
465                 470                 475                 480

Ala Leu Gln Met Leu Gly Ala His Leu Val Asp Glu Gly Phe Lys Glu
                485                 490                 495

Met Leu Ile Pro Thr Asn Ala Ala Ala Tyr Arg Arg Asn Tyr Ile Ala
            500                 505                 510

Thr Thr Thr Val
        515

(2) INFORMATION FOR SEQ ID NO: 3:

(i) SEQUENCE CHARACTERISTICS:
        (A) LENGTH: 1748 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Brassica napus
        (B) STRAIN: Westar
        (D) DEVELOPMENTAL STAGE: 14 day greening-etiolated
        (F) TISSUE TYPE: hypocotyls (vii) IMMEDIATE SOURCE:
        (A) LIBRARY: Tsang
        (B) CLONE: pDR111

(ix) FEATURE:
        (A) NAME/KEY: 5'UTR
        (B) LOCATION:1..18

(ix) FEATURE:
        (A) NAME/KEY: CDS
        (B) LOCATION:19..1575

(ix) FEATURE:
        (A) NAME/KEY: 3'UTR
        (B) LOCATION:1576..1748
```

(xi) SEQUENCE DESCRIPTION: SEQ ID NO: 3:

```
CCACGCGTCC GAAAAGAT ATG GAT ATG GCT TTT GTG GAA GTT TGT TTA CGG              51
                    Met Asp Met Ala Phe Val Glu Val Cys Leu Arg
                        520             525

ATG CTA CTT GTC TTC GTA CTG TCT TGG ACG ATA TTT CAC GTC AAC AAC              99
Met Leu Leu Val Phe Val Leu Ser Trp Thr Ile Phe His Val Asn Asn
530                 535                 540

AGG AAG AAG AAG AAG GCG ACG AAG TTG GCG GAT CTG GCT ACT GAG GAG             147
Arg Lys Lys Lys Lys Ala Thr Lys Leu Ala Asp Leu Ala Thr Glu Glu
545                 550                 555                 560

AGA AAA GAA GGT GGC CCT GAC GTC ATA ATA GTC GGA GCT GGA GTG GGC             195
Arg Lys Glu Gly Gly Pro Asp Val Ile Ile Val Gly Ala Gly Val Gly
                565                 570                 575

GGC TCA GCT CTC GCC TAT GCT CTT GCT AAG GAC GGG CGT CGA GTA CAT             243
Gly Ser Ala Leu Ala Tyr Ala Leu Ala Lys Asp Gly Arg Arg Val His
                580                 585                 590

GTG ATA GAA AGA GAC ATG AGA GAG CCA GTG AGA ATG ATG GGT GAG TTC             291
Val Ile Glu Arg Asp Met Arg Glu Pro Val Arg Met Met Gly Glu Phe
                595                 600                 605

ATG CAG CCA GGA GGA CGG CTC ATG CTT TCT AAG CTC GGT CTT CAA GAT             339
Met Gln Pro Gly Gly Arg Leu Met Leu Ser Lys Leu Gly Leu Gln Asp
    610                 615                 620

TGT TTA GAG GAA ATA GAC GCA CAG AAA TCC ACC GGC ATA AGA CTT TTT             387
Cys Leu Glu Glu Ile Asp Ala Gln Lys Ser Thr Gly Ile Arg Leu Phe
625                 630                 635                 640

AAG GAC GGA AAA GAA ACT GTC GCA TGT TTT CCG GTG GAC ACC AAC TTT             435
Lys Asp Gly Lys Glu Thr Val Ala Cys Phe Pro Val Asp Thr Asn Phe
                645                 650                 655

CCT TAT GAA CCA TCT GGT CGA TTT TTT CAC AAT GGC CGT TTT GTC CAG             483
Pro Tyr Glu Pro Ser Gly Arg Phe Phe His Asn Gly Arg Phe Val Gln
                660                 665                 670

AGA CTG CGC CAA AAG GCC TCT TCT CTT CCC AAT GTG CGG CTG GAA GAA             531
Arg Leu Arg Gln Lys Ala Ser Ser Leu Pro Asn Val Arg Leu Glu Glu
                675                 680                 685

GGG ACC GTC CGA TCT TTG ATA GAA GAA AAA GGA GTG GTC AAA GGA GTG             579
Gly Thr Val Arg Ser Leu Ile Glu Glu Lys Gly Val Val Lys Gly Val
                690                 695                 700

ACA TAC AAG AAC AGT TCA GGG GAA GAA ACC ACA TCA TTT GCA CCT CTC             627
Thr Tyr Lys Asn Ser Ser Gly Glu Glu Thr Thr Ser Phe Ala Pro Leu
705                 710                 715                 720

ACT GTC GTA TGC GAT GGT TGC CAC TCG AAC CTT CGT CGC TCT CTA AAT             675
Thr Val Val Cys Asp Gly Cys His Ser Asn Leu Arg Arg Ser Leu Asn
                725                 730                 735

GAC AAC AAT GCG GAG GTT ACG GCG TAC GAG ATT GGT TAC ATC TCG AGG             723
Asp Asn Asn Ala Glu Val Thr Ala Tyr Glu Ile Gly Tyr Ile Ser Arg
                740                 745                 750

AAT TGT CGC CTT GAA CAG CCC GAC AAG TTA CAC TTG ATA ATG GCT AAA             771
Asn Cys Arg Leu Glu Gln Pro Asp Lys Leu His Leu Ile Met Ala Lys
            755                 760                 765

CCG TCT TTC GCC ATG TTG TAT CAA GTC AGC AGC ACC GAC GTT CGT TGT             819
Pro Ser Phe Ala Met Leu Tyr Gln Val Ser Ser Thr Asp Val Arg Cys
            770                 775                 780

AAT TTT GAG CTT CTC TCC AAA AAT CTT CCT TCT GTT TCA AAT GGT GAA             867
Asn Phe Glu Leu Leu Ser Lys Asn Leu Pro Ser Val Ser Asn Gly Glu
785                 790                 795                 800

ATG ACG TCC TTC GTG AGG AAC TCT ATT GCT CCC CAG GTA CCT CTA AAA             915
Met Thr Ser Phe Val Arg Asn Ser Ile Ala Pro Gln Val Pro Leu Lys
    805                 810                 815

CTC CGC AAA ACA TTT TTG AAA GGG CTC GAT GAG GGA TCA CAT ATA AAA             963
```

```
Leu Arg Lys Thr Phe Leu Lys Gly Leu Asp Glu Gly Ser His Ile Lys
            820                 825                 830

ATT ACA CAA GCA AAG CGC ATC CCA GCT ACT TTG AGC AGA AAA AAG GGA      1011
Ile Thr Gln Ala Lys Arg Ile Pro Ala Thr Leu Ser Arg Lys Lys Gly
            835                 840                 845

GTG ATT GTG TTG GGA GAT GCA TTC AAC ATG CGT CAT CCC GTA ATC GCG      1059
Val Ile Val Leu Gly Asp Ala Phe Asn Met Arg His Pro Val Ile Ala
850                 855                 860

TCG GGG ATG ATG GTT TTA TTG TCT GAC ATT CTC ATT CTA AGC CGT CTT      1107
Ser Gly Met Met Val Leu Leu Ser Asp Ile Leu Ile Leu Ser Arg Leu
865                 870                 875                 880

CTC AAG CCT TTG GGC AAC CTC GGT GAT GAA AAC AAA GTC TCA GAA GTT      1155
Leu Lys Pro Leu Gly Asn Leu Gly Asp Glu Asn Lys Val Ser Glu Val
                885                 890                 895

ATG AAG TCC TTC TAT GCT CTA CGC AAG CCA ATG TCA GCA ACA GTA AAC      1203
Met Lys Ser Phe Tyr Ala Leu Arg Lys Pro Met Ser Ala Thr Val Asn
                900                 905                 910

ACA CTA GGG AAT TCA TTT TGG CAA GTG CTA ATT GCT TCA ACG GAC GAA      1251
Thr Leu Gly Asn Ser Phe Trp Gln Val Leu Ile Ala Ser Thr Asp Glu
                915                 920                 925

GCA AAA GAG GCC ATG CGA CAA GGT TGC TTT GAT TAC CTC TCT AGT GGT      1299
Ala Lys Glu Ala Met Arg Gln Gly Cys Phe Asp Tyr Leu Ser Ser Gly
930                 935                 940

GGG TTT CGC ACG TCA GGC TTG ATG GCT CTG ATT GGT GGC ATG AAC CCT      1347
Gly Phe Arg Thr Ser Gly Leu Met Ala Leu Ile Gly Gly Met Asn Pro
945                 950                 955                 960

AGG CCA CTT TCT CTC TTC TAT CAT CTA TTC GTT ATT TCT TTA TCC TCC      1395
Arg Pro Leu Ser Leu Phe Tyr His Leu Phe Val Ile Ser Leu Ser Ser
                965                 970                 975

ATT GGC CAA CTG CTC TCT CCA TTC CCC ACT CCT CTT CGT GTT TGG CAT      1443
Ile Gly Gln Leu Leu Ser Pro Phe Pro Thr Pro Leu Arg Val Trp His
                980                 985                 990

AGC CTC AGA CTT CTT GAT TTG TCT TTG AAA ATG TTG GTT CCT CAT CTC      1491
Ser Leu Arg Leu Leu Asp Leu Ser Leu Lys Met Leu Val Pro His Leu
            995                 1000                1005

AAG GCC GAA GGA ATA GGT CAA ATG TTG TCT CCA ACA AAT GCA GCG GCG      1539
Lys Ala Glu Gly Ile Gly Gln Met Leu Ser Pro Thr Asn Ala Ala Ala
            1010                1015                1020

TAT CGC AAA AGC TAT ATG GCT GCA ACC GTT GTC TAG ACATTGATGA           1585
Tyr Arg Lys Ser Tyr Met Ala Ala Thr Val Val
1025                1030                1035

AATATAGATG GTGCACAAAT CTTTGTGATT GTGGATTTGT GAAATAGTA TTGCAATATG    1645

TTACTGAAGA AACTTTTCCT TATCCACTTA TAAGTGGAAA TAGGAAGAAT GTGTATATAT  1705

GTAAGGGGTG ACAATTATTT TGAAATAAAA TTAAGAAAAT AAC                    1748

(2) INFORMATION FOR SEQ ID NO: 4:

(i) SEQUENCE CHARACTERISTICS:
        (A) LENGTH: 518 amino acids
        (B) TYPE: amino acid
        (D) TOPOLOGY: linear (ii) MOLECULE TYPE: protein (xi) SEQUENCE DESCRIPTION: SEQ ID NO: 4:

Met Asp Met Ala Phe Val Glu Val Cys Leu Arg Met Leu Leu Val Phe
1               5                   10                  15

Val Leu Ser Trp Thr Ile Phe His Val Asn Asn Arg Lys Lys Lys
            20                  25                  30
```

-continued

```
Ala Thr Lys Leu Ala Asp Leu Ala Thr Glu Glu Arg Lys Glu Gly Gly
         35                  40                  45

Pro Asp Val Ile Ile Val Gly Ala Gly Val Gly Ser Ala Leu Ala
 50                  55                  60

Tyr Ala Leu Ala Lys Asp Gly Arg Arg Val His Val Ile Glu Arg Asp
 65                  70                  75                  80

Met Arg Glu Pro Val Arg Met Met Gly Glu Phe Met Gln Pro Gly Gly
                 85                  90                  95

Arg Leu Met Leu Ser Lys Leu Gly Leu Gln Asp Cys Leu Glu Glu Ile
                100                 105                 110

Asp Ala Gln Lys Ser Thr Gly Ile Arg Leu Phe Lys Asp Gly Lys Glu
                115                 120                 125

Thr Val Ala Cys Phe Pro Val Asp Thr Asn Phe Pro Tyr Glu Pro Ser
    130                 135                 140

Gly Arg Phe Phe His Asn Gly Arg Phe Val Gln Arg Leu Arg Gln Lys
145                 150                 155                 160

Ala Ser Ser Leu Pro Asn Val Arg Leu Glu Glu Gly Thr Val Arg Ser
                165                 170                 175

Leu Ile Glu Glu Lys Gly Val Val Lys Gly Val Thr Tyr Lys Asn Ser
                180                 185                 190

Ser Gly Glu Glu Thr Thr Ser Phe Ala Pro Leu Thr Val Val Cys Asp
    195                 200                 205

Gly Cys His Ser Asn Leu Arg Arg Ser Leu Asn Asp Asn Asn Ala Glu
210                 215                 220

Val Thr Ala Tyr Glu Ile Gly Tyr Ile Ser Arg Asn Cys Arg Leu Glu
225                 230                 235                 240

Gln Pro Asp Lys Leu His Leu Ile Met Ala Lys Pro Ser Phe Ala Met
                245                 250                 255

Leu Tyr Gln Val Ser Ser Thr Asp Val Arg Cys Asn Phe Glu Leu Leu
                260                 265                 270

Ser Lys Asn Leu Pro Ser Val Ser Asn Gly Glu Met Thr Ser Phe Val
                275                 280                 285

Arg Asn Ser Ile Ala Pro Gln Val Pro Leu Lys Leu Arg Lys Thr Phe
    290                 295                 300

Leu Lys Gly Leu Asp Glu Gly Ser His Ile Lys Ile Thr Gln Ala Lys
305                 310                 315                 320

Arg Ile Pro Ala Thr Leu Ser Arg Lys Lys Gly Val Ile Val Leu Gly
                325                 330                 335

Asp Ala Phe Asn Met Arg His Pro Val Ile Ala Ser Gly Met Met Val
                340                 345                 350

Leu Leu Ser Asp Ile Leu Ile Leu Ser Arg Leu Leu Lys Pro Leu Gly
    355                 360                 365

Asn Leu Gly Asp Glu Asn Lys Val Ser Glu Val Met Lys Ser Phe Tyr
370                 375                 380

Ala Leu Arg Lys Pro Met Ser Ala Thr Val Asn Thr Leu Gly Asn Ser
385                 390                 395                 400

Phe Trp Gln Val Leu Ile Ala Ser Thr Asp Glu Ala Lys Glu Ala Met
                405                 410                 415

Arg Gln Gly Cys Phe Asp Tyr Leu Ser Ser Gly Gly Phe Arg Thr Ser
                420                 425                 430

Gly Leu Met Ala Leu Ile Gly Gly Met Asn Pro Arg Pro Leu Ser Leu
    435                 440                 445

Phe Tyr His Leu Phe Val Ile Ser Leu Ser Ser Ile Gly Gln Leu Leu
```

```
              450              455              460
Ser Pro Phe Pro Thr Pro Leu Arg Val Trp His Ser Leu Arg Leu Leu
465                 470                 475                 480

Asp Leu Ser Leu Lys Met Leu Val Pro His Leu Lys Ala Glu Gly Ile
                485                 490                 495

Gly Gln Met Leu Ser Pro Thr Asn Ala Ala Ala Tyr Arg Lys Ser Tyr
            500                 505                 510

Met Ala Ala Thr Val Val
        515

(2) INFORMATION FOR SEQ ID NO: 5:

(i) SEQUENCE CHARACTERISTICS:
        (A) LENGTH: 1893 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Bassica napus
        (B) STRAIN: Westar
        (D) DEVELOPMENTAL STAGE: 14 day greening-etiolated
        (F) TISSUE TYPE: hypocotyls (vii) IMMEDIATE SOURCE:
        (A) LIBRARY: Tsang
        (B) CLONE: pDR411

(ix) FEATURE:
        (A) NAME/KEY: 5'UTR
        (B) LOCATION:1..28

(ix) FEATURE:
        (A) NAME/KEY: exon
        (B) LOCATION:29..1466

(ix) FEATURE:
        (A) NAME/KEY: intron
        (B) LOCATION:1467..1623

(ix) FEATURE:
        (A) NAME/KEY: exon
        (B) LOCATION:1624..1697

(ix) FEATURE:
        (A) NAME/KEY: 3'UTR
        (B) LOCATION:1698..1893

(xi) SEQUENCE DESCRIPTION: SEQ ID NO: 5:

CCACGCGTCC GCGGACGCGT GGGCAGATAT GGATCTAGCT TTTCCGCACG TTTGTTTGTG      60

GACGCTACTC GCCTTTGTGC TGACTTGGAC AGTGTTCTAC GTCAACAACA GGAGGAAGAA     120

GGTGGCGAAG TTACCCGATG CGGCGACAGA GGTGAGAAGA GACGGTGATG CTGACGTCAT     180

CATCGTCGGA GCTGGTGTTG GAGGTTCAGC TCTCGCCTAC GCTCTTGCAA AGGATGGGCG     240

TCGAGTACAT GTGATAGAGA GGGACATGAG GGAACCAGTG AGAATGATGG GTGAATTTAT     300

GCAACCCGGT GGACGACTAC TGCTTTCTAA GCTTGGTCTT GAAGATTGTT TGGAGGGAAT     360

AGATGAACAG ATAGCCACAG GCTTAGCAGT TTATAAGGAC GGACAAAAAG CACTCGTGTC     420

TTTTCCAGAG GACAACGACT TTCCTTATGA ACCTACTGGT CGAGCTTTTT ATAATGGCCG     480

TTTTGTCCAG AGACTGCGCC AAAAGGCTTC TTCGCTCCCC ACTGTACAAC TTGAAGAAGG     540
```

```
GACTGTAAAA TCTTTGATAG AAGAAAAAGG AGTGATCAAA GGAGTGACAT ACAAGAATAG    600

TGCAGGCGAA GAAACGACTG CATTTGCACC TCTCACAGTG GTATGCGACG GTTGCTATTC    660

AAACCTTCGT CGGTCTGTTA ACGACAACAA TGCGGAGGTT ATATCGTACC AAGTTGGTTA    720

CGTCTCAAAG AATTGTCAGC TTGAAGATCC TGAAAAGTTA AAATTGATAA TGTCTAAACC    780

TTCCTTCACC ATGTTGTATC AAATAAGCAG CACCGATGTT CGTTGTGTTA TGGAGATTTT    840

CCCCGGCAAT ATTCCTTCTA TTTCAAATGG CGAAATGGCT GTTTATTTGA AAAATACTAT    900

GGCTCCTCAG GTACCTCCAG AACTCCGCAA AATATTTTTG AAAGGAATTG ATGAGGGAGC    960

ACAAATTAAA GCGATGCCAA CAAAGAGAAT GGAAGCTACT TTGAGCGAAA AGCAAGGAGT   1020

GATTGTGTTG GGAGATGCAT TCAACATGCG CCACCCAGCG ATTGCCTCTG GAATGATGGT   1080

TGTATTATCT GACATTCTCA TTCTACGCCG CCTTCTCCAG CCATTGCGAA ACCTCAGTGA   1140

TGCAAATAAA GTATCAGAAG TTATTAAGTC ATTTTATGTC ATCCGAAAGC CAATGTCAGC   1200

GACGGTGAAC ACGCTAGGAA ATGCATTTTC TCAAGTGCTA ATTGCATCTA CGGACGAAGC   1260

AAAAGAAGCG ATGCGACAAG GCTGTTTTGA TTACCTCTCT AGTGGCGGCT TTCGCACGTC   1320

AGGAATGATG GCTCTGCTCG GTGGCATGAA CCCTCGACCA CTCTCTCTCA TCTTTCATCT   1380

ATGTGGTATT ACTCTATCCT CCATTGGTCA ACTGCTCTCG CCATTTCCAT CTCCTCTTGG   1440

CATTTGGCAT AGCCTCAGAC TTTTTGGTGT AAGTCATTAT CTCCCTCCCT ATGTTATTTA   1500

CATATTTTTC TTTGTGTTAT ATATTTTGTA AATAATTTAC AATTGAATTT TGACATTTTC   1560

TTGTTGTTTA TGTGTATGCC TAATTGTCTA TGAAAATGTT GGTTCCTCAT CTTAAGGCTG   1620

AAGGGGTTAG CCAAATGCTG TCTCCAGCAT ACGCAGCCGC GTATCGCAAA AGCTATATGA   1680

CCGCAACCGC TCTCTAAGCA TCGATGATAA GAACCGCGAA TGATACTATG ACATATTTGG   1740

AGCGCTAGTA TTTTGTGGTT TTGCATCCGT TAAAAATTTA AAATGTGTTG CTGTGTGTTT   1800

ACTATTATTA GTGTATTACC TGGAAAATAC CCGTGGGTAT ATTCTAAATG TATAAAATAT   1860

TGTGATAAAT AAAACGACTC TCCGTTTGGT TGG                                1893
```

(2) INFORMATION FOR SEQ ID NO: 6:

(i) SEQUENCE CHARACTERISTICS:
        (A) LENGTH: 572 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Mus Musculus
        (B) STRAIN: B6CBA
        (D) DEVELOPMENTAL STAGE: 6-8 weeks
        (F) TISSUE TYPE: liver (vii) IMMEDIATE SOURCE:
        (A) LIBRARY: Lambda ZAP vector Stratagene catalog #935302
        (B) CLONE: pMMSE-17

(x) PUBLICATION INFORMATION:
        (A) AUTHORS: Kosuga, K.
            Hata, S.
            Osumi, T.
            Sakakibara, J.
            Ono, T.
        (B) TITLE: Nucleotide sequence of a cDNA for mouse
            squalene epoxidase
        (C) JOURNAL: Biochim. Biophys. Acta
        (D) VOLUME: 1260
        (E) ISSUE: 3
        (F) PAGES: 345-348

(G) DATE: 1995

(xi) SEQUENCE DESCRIPTION: SEQ ID NO: 6:

```
Met Trp Thr Phe Leu Gly Ile Ala Thr Phe Thr Tyr Phe Tyr Lys Lys
1               5                   10                  15

Cys Gly Asp Val Thr Leu Ala Asn Lys Glu Leu Leu Leu Cys Val Leu
                20                  25                  30

Val Phe Leu Ser Leu Gly Leu Val Leu Ser Tyr Arg Cys Arg His Arg
            35                  40                  45

His Gly Gly Leu Leu Gly Arg His Gln Ser Gly Ala Gln Phe Ala Ala
        50                  55                  60

Phe Ser Asp Ile Leu Ser Ala Leu Pro Leu Ile Gly Phe Phe Trp Ala
65                  70                  75                  80

Lys Ser Pro Glu Ser Glu Lys Lys Glu Gln Leu Glu Ser Lys Lys Cys
                85                  90                  95

Arg Lys Glu Ile Gly Leu Ser Glu Thr Thr Leu Thr Gly Ala Ala Thr
                100                 105                 110

Ser Val Ser Thr Ser Phe Val Thr Asp Pro Glu Val Ile Ile Val Gly
            115                 120                 125

Ser Gly Val Leu Gly Ser Ala Leu Ala Ala Val Leu Ser Arg Asp Gly
        130                 135                 140

Arg Lys Val Thr Val Ile Glu Arg Asp Leu Lys Glu Pro Asp Arg Ile
145                 150                 155                 160

Val Gly Glu Leu Leu Gln Pro Gly Gly Tyr Arg Val Leu Gln Glu Leu
                165                 170                 175

Gly Leu Gly Asp Thr Val Glu Gly Leu Asn Ala His Ile His Ile Gly
                180                 185                 190

Tyr Ile Val His Asp Tyr Glu Ser Arg Ser Glu Val Gln Ile Pro Tyr
            195                 200                 205

Pro Leu Ser Glu Thr Asn Gln Val Gln Ser Gly Ile Ala Phe His His
        210                 215                 220

Gly Arg Phe Ile Met Ser Leu Arg Lys Ala Ala Met Ala Glu Pro Asn
225                 230                 235                 240

Val Lys Phe Ile Glu Gly Val Val Leu Gln Leu Leu Glu Glu Asp Asp
                245                 250                 255

Ala Val Ile Gly Val Gln Tyr Lys Asp Lys Glu Thr Gly Asp Thr Lys
                260                 265                 270

Glu Leu His Ala Pro Leu Thr Val Val Ala Asp Gly Leu Phe Ser Lys
            275                 280                 285

Phe Arg Lys Ser Leu Ile Ser Ser Lys Val Ser Val Ser Ser His Phe
        290                 295                 300

Val Gly Phe Leu Met Lys Asp Ala Pro Gln Phe Lys Pro Asn Phe Ala
305                 310                 315                 320

Glu Leu Val Leu Val Asn Pro Ser Pro Val Leu Ile Tyr Gln Ile Ser
                325                 330                 335

Ser Ser Glu Thr Arg Val Leu Val Asp Ile Arg Gly Glu Leu Pro Arg
            340                 345                 350

Asn Leu Arg Glu Tyr Met Ala Glu Gln Ile Tyr Pro Gln Leu Pro Glu
        355                 360                 365

His Leu Lys Glu Ser Phe Leu Glu Ala Ser Gln Asn Gly Arg Leu Arg
        370                 375                 380

Thr Met Pro Ala Ser Phe Leu Pro Pro Ser Ser Val Asn Lys Arg Gly
385                 390                 395                 400
```

-continued

```
Val Leu Ile Leu Gly Asp Ala Tyr Asn Leu Arg His Pro Leu Thr Gly
                405                 410                 415
Gly Gly Met Thr Val Ala Leu Lys Asp Ile Lys Leu Trp Arg Gln Leu
            420                 425                 430
Leu Lys Asp Ile Pro Asp Leu Tyr Asp Asp Ala Ala Ile Phe Gln Ala
        435                 440                 445
Lys Lys Ser Phe Phe Trp Ser Arg Lys Arg Thr His Ser Phe Val Val
450                 455                 460
Asn Val Leu Ala Gln Ala Leu Tyr Glu Leu Phe Ser Ala Thr Asp Asp
465                 470                 475                 480
Ser Leu His Gln Leu Arg Lys Ala Cys Phe Leu Tyr Phe Lys Leu Gly
                485                 490                 495
Gly Glu Cys Val Thr Gly Pro Val Gly Leu Leu Ser Ile Leu Ser Pro
            500                 505                 510
His Pro Leu Val Leu Ile Arg His Phe Phe Ser Val Ala Ile Tyr Ala
        515                 520                 525
Thr Tyr Phe Cys Phe Lys Ser Glu Pro Trp Ala Thr Lys Pro Arg Ala
    530                 535                 540
Leu Phe Ser Ser Gly Ala Val Leu Tyr Lys Ala Cys Ser Ile Leu Phe
545                 550                 555                 560
Pro Leu Ile Tyr Ser Glu Met Lys Tyr Leu Val His
                565                 570

(2) INFORMATION FOR SEQ ID NO: 7:

(i) SEQUENCE CHARACTERISTICS:
        (A) LENGTH: 573 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Rattus norvegicus
        (F) TISSUE TYPE: kidney
        (H) CELL LINE: NRK (vii) IMMEDIATE SOURCE:
        (A) LIBRARY: pcD2 library of H. Okayama
        (B) CLONE: Tb-1

(x) PUBLICATION INFORMATION:
        (A) AUTHORS: Sakakibara, J.
            Watanabe, R.
            Kanai, R.
            Ono, T.
        (B) TITLE: Molecular cloning and expression of rat
            sqalene epoxidase
        (C) JOURNAL: J. Biol. Chem.
        (D) VOLUME: 270
        (E) ISSUE: 1
        (F) PAGES: 17-20
        (G) DATE: 1995

(xi) SEQUENCE DESCRIPTION: SEQ ID NO: 7:

Met Trp Thr Phe Leu Gly Ile Ala Thr Phe Thr Tyr Phe Tyr Lys Lys
1               5                   10                  15
Cys Gly Asp Val Thr Leu Ala Asn Lys Glu Leu Leu Leu Cys Val Leu
            20                  25                  30
Val Phe Leu Ser Leu Gly Leu Val Leu Ser Tyr Arg Cys Arg His Arg
```

-continued

```
             35                  40                  45
Asn Gly Gly Leu Leu Gly Arg His Gln Ser Gly Ser Gln Phe Ala Ala
 50                  55                  60
Phe Ser Asp Ile Leu Ser Ala Leu Pro Leu Ile Gly Phe Phe Trp Ala
65                   70                  75                  80
Lys Ser Pro Pro Glu Ser Glu Lys Lys Glu Gln Leu Glu Ser Lys Arg
                 85                  90                  95
Arg Arg Lys Glu Val Asn Leu Ser Glu Thr Thr Leu Thr Gly Ala Ala
                100                 105                 110
Thr Ser Val Ser Thr Ser Ser Val Thr Asp Pro Glu Val Ile Ile Ile
             115                 120                 125
Gly Ser Gly Val Leu Gly Ser Ala Leu Ala Thr Val Leu Ser Arg Asp
130                 135                 140
Gly Arg Thr Val Thr Val Ile Glu Arg Asp Leu Lys Glu Pro Asp Arg
145                 150                 155                 160
Ile Leu Gly Glu Cys Leu Gln Pro Gly Gly Tyr Arg Val Leu Arg Glu
                165                 170                 175
Leu Gly Leu Gly Asp Thr Val Glu Ser Leu Asn Ala His His Ile His
                180                 185                 190
Gly Tyr Val Ile His Asp Cys Glu Ser Arg Ser Glu Val Gln Ile Pro
            195                 200                 205
Tyr Pro Val Ser Glu Asn Asn Gln Val Gln Ser Gly Val Ala Phe His
210                 215                 220
His Gly Lys Phe Ile Met Ser Leu Arg Lys Ala Ala Met Ala Glu Pro
225                 230                 235                 240
Asn Val Lys Phe Ile Glu Gly Val Val Leu Arg Leu Leu Glu Glu Asp
                245                 250                 255
Asp Ala Val Ile Gly Val Gln Tyr Lys Asp Lys Glu Thr Gly Asp Thr
                260                 265                 270
Lys Glu Leu His Ala Pro Leu Thr Val Val Ala Asp Gly Leu Phe Ser
            275                 280                 285
Lys Phe Arg Lys Asn Leu Ile Ser Asn Lys Val Ser Val Ser Ser His
            290                 295                 300
Phe Val Gly Phe Ile Met Lys Asp Ala Pro Gln Phe Lys Ala Asn Phe
305                 310                 315                 320
Ala Glu Leu Val Leu Val Asp Pro Ser Pro Val Leu Ile Tyr Gln Ile
                325                 330                 335
Ser Pro Ser Glu Thr Arg Val Leu Val Asp Ile Arg Gly Glu Leu Pro
                340                 345                 350
Arg Asn Leu Arg Glu Tyr Met Thr Glu Gln Ile Tyr Pro Gln Ile Pro
            355                 360                 365
Asp His Leu Lys Glu Ser Phe Leu Glu Ala Cys Gln Asn Ala Arg Leu
            370                 375                 380
Arg Thr Met Pro Ala Ser Phe Leu Pro Pro Ser Ser Val Asn Lys Arg
385                 390                 395                 400
Gly Val Leu Leu Leu Gly Asp Ala Tyr Asn Leu Arg His Pro Leu Thr
                405                 410                 415
Gly Gly Gly Met Thr Val Ala Leu Lys Asp Ile Lys Ile Trp Arg Gln
                420                 425                 430
Leu Leu Lys Asp Ile Pro Asp Leu Tyr Asp Asp Ala Ala Ile Phe Gln
            435                 440                 445
Ala Lys Lys Ser Phe Phe Trp Ser Arg Lys Arg Ser His Ser Phe Val
450                 455                 460
```

```
Val Asn Val Leu Ala Gln Ala Leu Tyr Glu Leu Phe Ser Ala Thr Asp
465                 470                 475                 480

Asp Ser Leu Arg Gln Leu Arg Lys Ala Cys Phe Leu Tyr Phe Lys Leu
                485                 490                 495

Gly Gly Glu Cys Leu Thr Gly Pro Val Gly Leu Leu Ser Ile Leu Ser
                500                 505                 510

Pro Asp Pro Leu Leu Leu Ile Arg His Phe Phe Ser Val Ala Val Tyr
                515                 520                 525

Ala Thr Tyr Phe Cys Phe Lys Ser Glu Pro Trp Ala Thr Lys Pro Arg
                530                 535                 540

Ala Leu Phe Ser Ser Gly Ala Ile Leu Tyr Lys Ala Cys Ser Ile Ile
545                 550                 555                 560

Phe Pro Leu Ile Tyr Ser Glu Met Lys Tyr Leu Val His
                565                 570
```

(2) INFORMATION FOR SEQ ID NO: 8:

(i) SEQUENCE CHARACTERISTICS:
        (A) LENGTH: 496 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Saccharomyces cerevisiae
        (B) STRAIN: A2-M8

(x) PUBLICATION INFORMATION:
        (A) AUTHORS: Jandrositz, A.
            Hoegenauer, G.
            Turnowsky, F.
        (B) TITLE: The gene encoding squalene epoxidase from
            Saccharomyces cerevisiae: cloning and
            characterization
        (C) JOURNAL: Gene
        (D) VOLUME: 107
        (F) PAGES: 155-160
        (G) DATE: 1991

(xi) SEQUENCE DESCRIPTION: SEQ ID NO: 8:

```
Met Ser Ala Val Asn Val Ala Pro Glu Leu Ile Asn Ala Asp Asn Thr
1               5                   10                  15

Ile Thr Tyr Asp Ala Ile Val Ile Gly Ala Gly Val Ile Gly Pro Cys
                20                  25                  30

Val Ala Thr Gly Leu Ala Arg Lys Gly Lys Lys Val Leu Ile Val Glu
                35                  40                  45

Arg Asp Trp Ala Met Pro Asp Arg Ile Val Gly Glu Leu Met Gln Pro
    50                  55                  60

Gly Gly Val Arg Ala Leu Arg Ser Leu Gly Met Ile Gln Ser Ile Asn
65                  70                  75                  80

Asn Ile Glu Ala Tyr Pro Val Thr Gly Tyr Thr Val Phe Phe Asn Gly
                85                  90                  95

Glu Gln Val Asp Ile Pro Tyr Pro Tyr Lys Ala Asp Ile Pro Lys Val
                100                 105                 110

Glu Lys Leu Lys Asp Leu Val Lys Asp Gly Asn Asp Lys Val Leu Glu
                115                 120                 125
```

```
Asp Ser Thr Ile His Ile Lys Asp Tyr Glu Asp Glu Arg Glu Arg
    130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175

Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
    210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Phe Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
        275                 280                 285

Lys Asp Val Gln Pro Phe Ile Pro Lys Ser Leu Arg Pro Ser Phe Asp
    290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Met Thr Val Gly Leu
            340                 345                 350

His Asp Val Val Leu Leu Ile Lys Lys Ile Gly Asp Leu Asp Phe Ser
        355                 360                 365

Asp Arg Glu Lys Val Leu Asp Glu Leu Leu Asp Tyr His Phe Glu Arg
    370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
            420                 425                 430

Phe Leu Ser Gly Val Leu Pro Lys Pro Leu Gln Leu Thr Arg Val Phe
        435                 440                 445

Phe Ala Val Ala Phe Tyr Thr Ile Tyr Leu Asn Met Glu Glu Arg Gly
    450                 455                 460

Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
                485                 490                 495
```

(2) INFORMATION FOR SEQ ID NO: 9:

(i) SEQUENCE CHARACTERISTICS:
        (A) LENGTH: 536 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:
         (A) ORGANISM: Arabidopsis thaliana
         (B) STRAIN: Columbia
         (D) DEVELOPMENTAL STAGE: 4 different stages and tissues (vii) IMMEDIATE SOURCE:
         (A) LIBRARY: Lambda-PRL2
         (B) CLONE: 250F2T7

(x) PUBLICATION INFORMATION:
         (A) AUTHORS: Newman, T.
             deBruijn, F. J.
             Green, P.
             Keegstra, K.
             Kende, H.
             McIntosh, L.
             Ohlrogge, J.
             Raikhel, N.
             Somerville, S.
             Thomashow, M.
         (B) TITLE: Genes galore: a summary of methods for
             accessing results from large-scale partial
             sequencing of anonymous Arabidopsis cDNA clones
         (C) JOURNAL: Plant Physiol.
         (D) VOLUME: 106
         (F) PAGES: 1241-1255
         (G) DATE: 1994

(xi) SEQUENCE DESCRIPTION: SEQ ID NO: 9:

GAGAACATAT AAAAGCCATG CCAACAAAGA AGATGACAGC TACTTTGAGC GAGAAGAAAG      60

GAGTGATTTT ATTGGGAGAT GCATTCAACA TGCGTCATCC AGCAATCGCA TCTGGAATGA     120

TGGTTTTATT ATCTGACATT CTCATTCTAC GCCGTCTTCT CCAGCCATTA AGCAACCTTG     180

GCAATGCGCA AAAAATCTCA CAAGTTATCA AGTCCTTTTA TGATATCCGC AAGCCAATGT     240

CAGCGACAGT TAACACGTTA GGAAATGCAT TCTCTCAAGT GCTAGTTGCA TCGACGGACG     300

AAGCAAAAGA GGCAATGAGA CAAGGTTGCT ATGATTACCT CTCTAGTGGT GGGTTTCGCA     360

CGTCAGGGAT GATGGCTTTG CTAGGCGGAT GAACCCTCGT CCGATCTCTC NCATCNANCA     420

NCNAGGGGAA CACNCANCCC CATNGGCATC AACNCCNCAT TCCCNNCCCT TCGATTGGAA     480

CCTCGACTTT TGGTGGNNNA AAGGTGGCCC CCCANGGGAA GGTTCCATNT NTCCNC        536

(2) INFORMATION FOR SEQ ID NO: 10:

(i) SEQUENCE CHARACTERISTICS:
         (A) LENGTH: 540 base pairs
         (B) TYPE: nucleic acid
         (C) STRANDEDNESS: double
         (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: Ricinus Communis
         (B) STRAIN: Baker 296
         (D) DEVELOPMENTAL STAGE: immature castor fruits
         (F) TISSUE TYPE: endosperm and embryo (vii) IMMEDIATE SOURCE:
         (A) LIBRARY: lambdaZAPST
         (B) CLONE: pcrs547

(x) PUBLICATION INFORMATION:
         (A) AUTHORS: van de Loo, F. J.
             Turner, S.

Somerville, C.
(B) TITLE: Expressed sequence tags from developing castor seeds
(C) JOURNAL: Plant Physiol.
(D) VOLUME: 108
(F) PAGES: 1141-1150
(G) DATE: 1995

(xi) SEQUENCE DESCRIPTION: SEQ ID NO: 10:

```
TTTGAGCTCA GAGTCACAGA TATAGACATC CTAGGGAAAA CATTCTCCTA TAAACTAAAG    60
CGTATTACAA TTCACACTTC TTTTCCCCTC AACTTTGATT TGAACAAAGG GATGAGATTA   120
AAACCAAAAT GAGAAACGCC CCGTTCCTTC TTGTCACGAA TTTTTCACTC ACATTCTTGT   180
CAAACTAATT GCATTCAACA GGAGGAGCTC TATAATATGC TGGGACGGTT GCGGGGAAGA   240
ACATCTGTCT AACTCCTTCT GCCTTGATAA TGGGGAAGAT GATTCCTGAT GCACCCGATA   300
TCAACCTAGC TCCAACCCAG ACGCGCTTAG GTGAAGGGAA TGGCAGTAAC AAAGGGGGGG   360
CCCGGTACCC AATTTGCCCT ATAGTGAGCC GTATTCAATN ACTGGCCGTT GTTTCAACGT   420
GTGCCTTGGG AAACCCTGGG GTNCCACTTA TTGCTTCAGA CATCCCCTTT GCANTTGGTA   480
TTNGAGGGGC CGACCGTTGC CTCCAANAGT NCNCGTTNAA TTGGGTTGAA ANTTNCGGGA   540
```

(2) INFORMATION FOR SEQ ID NO: 11:

(i) SEQUENCE CHARACTERISTICS:
(A) LENGTH: 503 amino acids
(B) TYPE: amino acid
(D) TOPOLOGY: linear (ii) MOLECULE TYPE: protein (xi) SEQUENCE DESCRIPTION: SEQ ID NO: 11:

```
Met Asp Leu Ala Phe Pro His Val Cys Leu Trp Thr Leu Leu Ala Phe
1               5                   10                  15

Val Leu Thr Trp Thr Val Phe Tyr Val Asn Asn Arg Arg Lys Lys Val
            20                  25                  30

Ala Lys Leu Pro Asp Ala Ala Thr Glu Val Arg Arg Asp Gly Asp Ala
        35                  40                  45

Asp Val Ile Ile Val Gly Ala Gly Val Gly Gly Ser Ala Leu Ala Tyr
50                  55                  60

Ala Leu Ala Lys Asp Gly Arg Arg Val His Val Ile Glu Arg Asp Met
65                  70                  75                  80

Arg Glu Pro Val Arg Met Met Gly Glu Phe Met Gln Pro Gly Gly Arg
                85                  90                  95

Leu Leu Leu Ser Lys Leu Gly Leu Glu Asp Cys Leu Glu Gly Ile Asp
            100                 105                 110

Glu Gln Ile Ala Thr Gly Leu Ala Val Tyr Lys Asp Gly Gln Lys Ala
        115                 120                 125

Leu Val Ser Phe Pro Glu Asp Asn Asp Phe Pro Tyr Glu Pro Thr Gly
130                 135                 140

Arg Ala Phe Tyr Asn Gly Arg Phe Val Gln Arg Leu Arg Gln Lys Ala
145                 150                 155                 160

Ser Ser Leu Pro Thr Val Gln Leu Glu Glu Gly Thr Val Lys Ser Leu
                165                 170                 175

Ile Glu Glu Lys Gly Val Ile Lys Gly Val Thr Tyr Lys Asn Ser Ala
            180                 185                 190

Gly Glu Glu Thr Thr Ala Phe Ala Pro Leu Thr Val Val Cys Asp Gly
        195                 200                 205
```

-continued

```
Cys Tyr Ser Asn Leu Arg Arg Ser Val Asn Asp Asn Asn Ala Glu Val
    210                 215                 220

Ile Ser Tyr Gln Val Gly Tyr Val Ser Lys Asn Cys Gln Leu Glu Asp
225                 230                 235                 240

Pro Glu Lys Leu Lys Leu Ile Met Ser Lys Pro Ser Phe Thr Met Leu
            245                 250                 255

Tyr Gln Ile Ser Ser Thr Asp Val Arg Cys Val Met Glu Ile Phe Pro
            260                 265                 270

Gly Asn Ile Pro Ser Ile Ser Asn Gly Glu Met Ala Val Tyr Leu Lys
            275                 280                 285

Asn Thr Met Ala Pro Gln Val Pro Pro Glu Leu Arg Lys Ile Phe Leu
            290                 295                 300

Lys Gly Ile Asp Glu Gly Ala Gln Ile Lys Ala Met Pro Thr Lys Arg
305                 310                 315                 320

Met Glu Ala Thr Leu Ser Glu Lys Gln Gly Val Ile Val Leu Gly Asp
            325                 330                 335

Ala Phe Asn Met Arg His Pro Ala Ile Ala Ser Gly Met Met Val Val
            340                 345                 350

Leu Ser Asp Ile Leu Ile Leu Arg Arg Leu Leu Gln Pro Leu Arg Asn
        355                 360                 365

Leu Ser Asp Ala Asn Lys Val Ser Glu Val Ile Lys Ser Phe Tyr Val
        370                 375                 380

Ile Arg Lys Pro Met Ser Ala Thr Val Asn Thr Leu Gly Asn Ala Phe
385                 390                 395                 400

Ser Gln Val Leu Ile Ala Ser Thr Asp Glu Ala Lys Glu Ala Met Arg
            405                 410                 415

Gln Gly Cys Phe Asp Tyr Leu Ser Ser Gly Gly Phe Arg Thr Ser Gly
            420                 425                 430

Met Met Ala Leu Leu Gly Gly Met Asn Pro Arg Pro Leu Ser Leu Ile
            435                 440                 445

Phe His Leu Cys Gly Ile Thr Leu Ser Ser Ile Gly Gln Leu Leu Ser
        450                 455                 460

Pro Phe Pro Ser Pro Leu Gly Ile Trp His Ser Leu Arg Leu Phe Gly
465                 470                 475                 480

Val Ser Gln Met Leu Ser Pro Ala Tyr Ala Ala Ala Tyr Arg Lys Ser
            485                 490                 495

Tyr Met Thr Ala Thr Ala Leu
            500
```

REFERENCES

Anonymous(1995) Developments in Calgene's plant oils unit. *Biotech. Rep.* (July) :3

Altschul, S. F., Gish, W., Miller, W., Myers, E. W. and Lipman, D. J. (1990) Basic local alignment search tool. *J. Mol. Biol.* 215, 403–410.

Ausubel F M, Brent R, Kingston R E, Moore D D, Seidman J G, Smith J A, Struhl K, Albright L M, Coen D M, Varki A (eds) (1994) Current Protocols in Molecular Biology. John Wiley & Sons.

Barinaga, M. (1993) Ribozymes: killing the messenger. *Science* 262, 1512–1514.

Bechtold, N., Ellis, J., and Pelletier, G. (1993) In planta *Agrobacterium*-mediated gene transfer by infiltration of adult *Arabidopsis thaliana* plants. *C R Acad Sci Paris, Sciences de la vie/Life sciences* 316: 1194–1199.

Beltz, G. A., Jacobs, K. A., Eickbush, T. H., Cherbas, P. T. and Kafatos, F. C. (1983) Isolation of multigene families and determination of homologies by filter hybridization. *Meth. Enzymol.* 100, 266–285.

Bevan, M. (1984) Binary Agrobacterium Vectors for Plant Transformation. *Nucl. Acids Res.* 12, 8711–8721.

Bondioli, P., Mariani, C., Lanzani, A., Fedeli, E., Mossa, A. and Muller, A. (1992) Lampante olive oil refining with supercritical carbon dioxide. *J. Am. Oil Chem. Soc.* 69, 477–480.

Bondioli, P., Mariani, C., Lanzani, A., Fedeli, E. and Muller, A. (1993) Squalene recovery from olive oil deodorizer distillates. *J. Am. Oil Chem. Soc.* 70, 763–766.

Bourque, J. E. (1995) Antisense strategies for genetic manipulations in plants. *Plant Sci.* 105, 125–149.

Chappell, J., Saunders, C. A. and Wolf, F. R. inventors Amoco Corp. (1994) Process and composition for increasing squalene and sterol accumulation in higher plants. U.S. Pat. No. 5349126.

Christou, P. (1993) Particle gun mediated transformation. Curr. Opin. Biotech. 4, 135–141.

Datla, R. S. S., Hammerlindl, J. K., Panchuk, B., Pelcher, L. and Keller, W. (1992) Modified binary plant transformation vectors with the wild-type gene encoding NPTII. Gene 122, 383–384.

DeBlock, M., DeBrouwer, D., and Tenning, P. (1989) Transformation of *Brassica napus* and *Brassica oleracea* using *Agrobacterium tumefaciens* and the expression of the bar and neo genes in the transgenic plants. *Plant Physiol.* 91: 694–701.

Deprez, P. P., Volkman, J. K. and Davenport, S. R. (1990) Squalene content and neutral lipid composition of livers from deep-sea sharks caught in Tasmanian waters. *Aust. J. Mar. Freshwater Res.* 41, 375–387.

Goodall, G. J. and Filipowicz, W. (1991) Different effects of intron nucleotide composition and secondary structure on pre-mRNA splicing in monocot and dicot plants. *EMBO J.* 10, 2635–2644.

Guerineau, F. and Mullineaux, P. (1993) Plant Transformation and Expression Vectors. In: Croy, R. R. D. (Ed.) Plant Molecular Biology Labfax, pp. 121–147. Oxford: Bios Scientific.

Inouye, M. (1993) Regulation of gene expression by employing translational inhibition of mRNA utilizing interfering complementary DNA. U.S. Pat. No. 5,190,931.

Jandrositz, A., Turnowsky, F. and Hoegenauer, G. (1991) The gene encoding squalene epoxidase from *Saccharomyces cerevisiae*: cloning and characterization. *Gene* 107, 155–160.

Jorgensen, R. (1990) Altered gene expression in plants due to trans interactions between homologous genes. Trends Biotech. 8, 340–344.

Josefsson, L. -G., Lenman, M., Ericson, M. L. and Rask, L. (1987) Structure of a gene encoding the 1.7S storage protein, napin, from *Brassica napus*. *J. Biol. Chem.* 262, 12196–12201.

Kaiya, A. (1990) The use of natural squalene and squalane, and the latest situation of the raw materials. *Yukagaku* 39, 525–529.

Katavic, V., Haughn, G. W., Reed, D., Martin, M. and Kunst, L. (1994) In planta transformation of *Arabidopsis thaliana*. *Mol. Gen. Genet.* 245, 363–370

Katavic, V., Reed, D. W., Taylor, D. C., Giblin, E. M., Barton, D. L., Zou, J., MacKenzie, S. L., Covello, P. S. and Kunst, L. (1995) Alteration of seed fatty acid composition by an ethyl methanesulfonate-induced mutation in *Arabidopsis thaliana* affecting diacylglycerol acyltransferase activity. *Plant Physiol.* 108, 399–409.

Koncz, C. and Schell, J. (1986) The promoter of $T_L$-DNA gene 5 controls the tissue-specific expression of chimeric genes by a novel type of Agrobacterium binary vector. *Mol. Gen. Genet.* 204: 383–396.

Matzke, M. A. and Matzke, A. J. M. (1995) Homology-dependent gene silencing in transgenic plants: what does it really tell us? *Trends Genet.* 11, 1–3.

Meyer, P.(ed.) (1995) *Gene Silencing in Higher Plants and Related Phenomena in Other Eukaryotes*, Berlin: Springer.

Moloney, M. M., Walker, J. M. and Sharma, K. K. (1989) High efficiency transformation of *Brassica napus* using Agrobacterium vectors. *Plant Cell Reports*, 8: 238–242.

Murphy, D. J. (1996) Engineering oil production in rapeseed and other oil crops. *Trends Biotech.* 14, 206–213.

Ramamurthi, S. (1994): "Reaction Kinetics and Potential Application of Lipase-catalyzed Esterification of Fatty Acids with Methanol," University of Saskatwhewan, Ph.D.

Sakakibara, J., Watanabe, R., Kanai, Y. and Ono, T. (1995) Molecular cloning and expression of rat squalene epoxidase. *J. Biol. Chem.* 270, 17–20.

Stam, M., Mol, J. N. M. and Kooter, J. M. (1997) The silence of genes in transgenic plants. *Annals of Botany* 79, 3–12.

Steinecke, P., Herget, T. and Schreier, P. H. (1992) Expression of a chimeric ribozyme gene results in endonucleolytic cleavage of target mRNA and a concomitant reduction of gene expression in vivo. EMBO J. 11, 1525–1530.

Thomas, C. M., Jagura-Burdzy, G., Williams, D. R., Shah, D. and Thorsted, P. B. (1992) Replication, Maintenance and Transfer of Promiscuous IncP Plasmids. In: Balla, E. (Ed.) DNA Transfer and Gene Expression in Microorganisms, pp. 85–96. Andover: Intercept Ltd.

Wegener, D., Steinecke, P., Herget, T., Petereit, I., Philipp, C. and Schreier, P. H. (1994) Expression of a reporter gene is reduced by a ribozyme in transgenic plants. Mol. Gen. Genet. 245, 465–470.

Wierenga, R. K., Terpstra, P. and Hol, W. G. J. (1986) Prediction of the occurrence of the ADP-binding beta-alpha-beta-fold in proteins, using an amino acid sequence fingerprint. *J Mol. Biol.* 187, 101–107.

Yamamoto, T. and Kadowaki, Y. (1995) Superfamilies of protooncogenes: homology cloning and characterization of related members. Meth. Enzymol. 254, 169–183.

Yates, P. J., Haughan, P. A., Lenton, J. R. and Goad, L. J. (1991) Effects of terbinafine on growth, squalene, and steryl ester contents of a celery suspension culture. *Pesticide Biochem. Physiol.* 40, 221–226.

Zhao, J. J. and Pick, L. (1993) Generating loss-of-function phenotypes of the fushi tarazu gene with a targeted ribozyme in Drosophila. Nature 365, 448–451.

The teachings of the above references are specifically incorporated herein by reference.

What is claimed is:

1. An isolated and cloned DNA encoding squalene epoxidase having an amino acid sequence with at least 60% similarity to SEQ ID NO:2, SEQ ID NO:4 or SEQ ID NO:11.

2. The DNA according to claim 1, comprising a sequence having at least 60% identity to a specific sequence selected from the group consisting of SEQ ID NO:1, SEQ ID NO:3 and SEQ ID NO:5.

3. An isolated DNA encoding squalene epoxidase having an amino acid sequence selected from the group consisting of SEQ ID NO:2, SEQ ID NO:4 and SEQ ID NO:11.

4. An isolated DNA having the nucleotide sequence of SEQ ID NO:1.

5. An isolated DNA having the nucleotide sequence of SEQ ID NO:3.

6. An isolated DNA having the nucleotide sequence of SEQ ID NO:5.

7. An isolated and cloned DNA encoding squalene epoxidase from a plant species of the family Brassicaceae.

8. The plasmid pDR411 (ATCC 97845).

9. The plasmid pDR111 (ATCC 97846).

10. The plasmid p129F12T7 (ATCC 97847).

11. A vector for introducing a nucleotide sequence into a plant genome, wherein said vector comprises a transcriptional promoter, a nucleotide sequence that is antisense to a gene encoding squalene epoxidase having an amino acid sequence with at least 60% similarity to SEQ ID NO:2, SEQ ID NO:4 or SEQ ID NO:11, and a transcription terminator, all operably linked.

12. The vector according to claim 11, wherein said nucleotide sequence is antisense to a squalene epoxidase gene having at least 60% identity to SEQ ID NO:1, SEQ ID NO:3 and SEQ ID NO:5.

13. The vector pSE129A (ATCC 97910).

14. The vector pSE411A (ATCC 97908).

15. The vector pSE111A (ATCC 97909).

16. A vector for introducing a nucleotide sequence into a plant genome, wherein said vector comprises a transcriptional promoter, a nucleotide sequence, and a transcription terminator, all operably linked, wherein said nucleotide sequence encodes a squalene epoxidase having an amino acid sequence selected from the group consisting of SEQ ID NO:2, SEQ ID NO:4 and SEQ ID NO:11.

17. A process of producing a genetically-modified plant, comprising introducing into the genome of a plant at least one heterologous DNA sequence encoding squalene epoxidase having an amino acid sequence with at least 60% similarity to SEQ ID NO:2, SEQ ID NO:4 or SEQ ID NO:11, whereby the plant genome is modified to suppress squalene epoxidase expression by said plant and thereby increase squalene levels above squalene levels of a corresponding wild-type plant.

18. The process according to claim 17, wherein said at least one heterologous DNA sequence has at least 60% identity to a specific sequence selected from the group consisting of SEQ ID NO:1, SEQ ID NO:3 and SEQ ID NO:5.

19. The process as claimed in claim 17, wherein said at least one heterologous DNA sequence is in the sense orientation such that said at least one heterologous DNA sequence decreases expression of squalene epoxidase by said plant by co-suppression or homology-dependent gene silencing.

20. The process as claimed in claim 17, wherein said at least one heterologous DNA sequence is obtained by cloning.

21. The process according to claim 17, wherein said introducing of said at least one heterologous DNA sequence is carried out by a procedure selected from the group consisting of Agrobacterium-mediated transformation and particle gun transformation.

22. A process of producing a genetically-modified plant, comprising introducing a nucleotide sequence that reduces or prevents expression of squalene epoxidase into the genome of a plant, wherein said nucleotide sequence comprises a transcriptional promoter and an operably linked sequence antisense to at least one squalene epoxidase messenger RNA encoding squalene epoxidase having an amino acid sequence with at least 60% similarity to SEQ ID NO:2, SEQ ID NO:4 or SEQ ID NO:11, whereby the plant genome is modified to suppress squalene epoxidase expression by said plant and thereby increase squalene levels in the modified plant above squalene levels of corresponding wild-type plants.

23. The process according to claim 22, wherein said nucleotide sequence has at least 60% identity to SEQ ID NO:1, SEQ ID NO:3 or SEQ ID NO:5.

24. A genetically-modified plant of the family Brassicaceae that accumulates squalene at levels higher than a corresponding wild-type plant, wherein said genetically-modified plant is produced by the process of claim 17.

25. A seed of a genetically-modified oilseed plant of the family Brassicaceae containing squalene at levels higher than seeds of corresponding wild-type plants, wherein said seed is from a genetically-modified oilseed plant that is produced by the process of claim 17.

26. A process of producing squalene, comprising growing the genetically-modified plant as defined in claim 24, harvesting said genetically-modified plant or seeds of said plant, and extracting squalene from said genetically-modified plant or seeds.

27. A genetically-modified plant of the family Brassicaceae having a genome comprising one or more DNA sequences comprising in operable linkage, a transcriptional promoter, a heterologous gene encoding squalene epoxidase and a transcription terminator, wherein said squalene epoxidase has an amino acid sequence selected from the group consisting of SEQ ID NO:2, SEQ ID NO:4 and SEQ ID NO:11.

28. The plant of claim 27 being of the genus Arabidopsis.

29. The plant of claim 27 being of the species *Arabidopsis thaliana*.

30. The plant of claim 27 being of the genus Brassica.

31. The plant of claim 30 being of the species *Brassica napus*.

32. A seed of a genetically-modified plant of the family Brassicaceae having a genome comprising one or more DNA sequences comprising in operable linkage, a transcriptional promoter, a heterologous gene encoding squalene epoxidase, and a transcription terminator, wherein said squalene epoxidase has an amino acid sequence selected from the group consisting of SEQ ID NO:2, SEQ ID NO:4 and SEQ ID NO:11.

33. The seed of claim 32 being of the genus Arabidopsis.

34. The seed of claim 33 being of the species *Arabidopsis thaliana*.

35. The seed of claim 32 being of the genus Brassica.

36. The seed of claim 35 being of the species *Brassica napus*.

37. A process of producing a genetically-modified plant, comprising introducing into the genome of a plant at least one heterologous DNA sequence encoding squalene epoxidase from a plant species of the family Brassicaceae.

38. A process of producing a genetically-modified plant, comprising introducing a nucleotide sequence that reduces or prevents expression of squalene epoxidase into the genome of a plant, wherein said nucleotide sequence comprises a transcriptional promoter and an operably linked sequence antisense to at least one squalene epoxidase messenger RNA encoding squalene epoxidase from a plant of the family Brassicaceae, whereby the plant genome is modified to suppress squalene epoxidase expression by said plant and thereby increase squalene levels in the modified plant above squalene levels of corresponding wild-type plants.

39. A genetically-modified plant of the family Brassicaceae that accumulates squalene at levels higher than a corresponding wild-type plant, wherein said genetically-modified plant is produced by the process of claim 37.

40. A seed of a genetically-modified plant of the family Brassicaceae that accumulates squalene at levels higher than seeds of corresponding wild-type plants, wherein said genetically modified plant is produced by the process of claim 37.

41. A process of producing squalene, comprising growing the genetically-modified plant of claim 39, harvesting said genetically modified plant or seeds of said plant, and extracting squalene from said genetically-modified plant or seeds.

* * * * *